(12) United States Patent
Fu et al.

(10) Patent No.: US 11,220,685 B2
(45) Date of Patent: Jan. 11, 2022

(54) MOLECULAR INDEXING OF INTERNAL SEQUENCES

(71) Applicant: Cellular Research, Inc., San Jose, CA (US)

(72) Inventors: Glenn Fu, San Jose, CA (US); Eleen Shum, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/836,750

(22) Filed: Mar. 31, 2020

(65) Prior Publication Data

US 2020/0332284 A1 Oct. 22, 2020

Related U.S. Application Data

(63) Continuation of application No. 15/596,364, filed on May 16, 2017, now Pat. No. 10,640,763.

(60) Provisional application No. 62/343,574, filed on May 31, 2016.

(51) Int. Cl.
| | | |
|---|---|---|
| *C12N 15/10* | (2006.01) | |
| *C12Q 1/6806* | (2018.01) | |
| *C12Q 1/6874* | (2018.01) | |
| *C12Q 1/6844* | (2018.01) | |

(52) U.S. Cl.
CPC ....... *C12N 15/1065* (2013.01); *C12Q 1/6806* (2013.01); *C12Q 1/6844* (2013.01); *C12Q 1/6874* (2013.01)

(58) Field of Classification Search
None
See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |

(Continued)

FOREIGN PATENT DOCUMENTS

| | | |
|---|---|---|
| CA | 2474509 | 2/2003 |
| DE | 102008025656 | 12/2009 |

(Continued)

OTHER PUBLICATIONS

Sun et al., "Ultra-deep profiling of alternatively spliced *Drosophila dscam* isoforms by circularization-assisted multi-segment sequencing," EMBO J. 2013, 32:2029-2038. (Year: 2013).*

(Continued)

*Primary Examiner* — Kaijiang Zhang
(74) *Attorney, Agent, or Firm* — Sheppard, Mullin, Richter & Hampton LLP

(57) ABSTRACT

The present disclosure relates to compositions, methods and kits for labeling an internal sequence of a target nucleic acid molecule with molecular barcodes. In some embodiments, the methods comprise intramolecular circulation of a labeled target nucleic acid molecule. Further provided methods for generating sequencing libraries comprising overlapping fragments covering the full length of a target nucleic acid molecule, sequencing the libraries using the methods disclosed herein, and methods of analyzing sequencing results therefrom.

19 Claims, 4 Drawing Sheets

Specification includes a Sequence Listing.

(56) References Cited

U.S. PATENT DOCUMENTS

| | | |
|---|---|---|
| 5,200,314 A | 4/1993 | Urdea |
| 5,308,990 A | 5/1994 | Takahashi et al. |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,181,582 B2 | 11/2015 | Kurn |
| 9,228,229 B2 | 1/2016 | Olson et al. |
| 9,262,376 B2 | 2/2016 | Tsuto |
| 9,290,808 B2 | 3/2016 | Fodor et al. |
| 9,290,809 B2 | 3/2016 | Fodor et al. |
| 9,297,047 B2 | 3/2016 | Furchak et al. |
| 9,315,857 B2 | 4/2016 | Fu et al. |
| 9,371,598 B2 | 6/2016 | Chee |
| 9,567,645 B2 | 2/2017 | Fan et al. |
| 9,567,646 B2 | 2/2017 | Fan et al. |
| 9,582,877 B2 | 2/2017 | Fu et al. |
| 9,593,365 B2 | 3/2017 | Frisen et al. |
| 9,598,736 B2 | 3/2017 | Fan et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,695,468 B2 | 7/2017 | Hindson et al. |

(56) References Cited

U.S. PATENT DOCUMENTS

| | | |
|---|---|---|
| 9,708,659 B2 | 7/2017 | Fodor et al. |
| 9,727,810 B2 | 8/2017 | Fodor et al. |
| 9,787,810 B1 | 10/2017 | Chiang |
| 9,816,137 B2 | 11/2017 | Fodor et al. |
| 9,845,502 B2 | 12/2017 | Fodor et al. |
| 9,850,515 B2 | 12/2017 | McCoy et al. |
| 9,856,530 B2 | 1/2018 | Hindson et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,002,316 B2 | 6/2018 | Fodor et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,047,394 B2 | 8/2018 | Fodor et al. |
| 10,059,991 B2 | 8/2018 | Fodor et al. |
| 10,131,958 B1 | 11/2018 | Fan et al. |
| 10,138,518 B2 | 11/2018 | Chun |
| 10,151,003 B2 | 12/2018 | Fan et al. |
| 10,202,641 B2 | 2/2019 | Shum |
| 10,202,646 B2 | 2/2019 | Fodor et al. |
| 10,208,343 B2 | 2/2019 | Hindson et al. |
| 10,208,356 B1 | 2/2019 | Fan et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,253,375 B1 | 4/2019 | Fan et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,301,677 B2 | 5/2019 | Shum et al. |
| 10,308,982 B2 | 6/2019 | Chee |
| 10,323,278 B2 | 6/2019 | Belgrader et al. |
| 10,337,061 B2 | 7/2019 | Hindson et al. |
| 10,338,066 B2 | 7/2019 | Fan et al. |
| 10,344,329 B2 | 7/2019 | Hindson et al. |
| 10,392,661 B2 | 8/2019 | Fodor et al. |
| 10,450,607 B2 | 10/2019 | Hindson et al. |
| 10,550,429 B2 | 2/2020 | Harada et al. |
| 10,619,186 B2 | 4/2020 | Betts et al. |
| 10,619,203 B2 | 4/2020 | Fodor et al. |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0094116 A1 | 7/2002 | Forst et al. |
| 2002/0106666 A1 | 8/2002 | Hayashizaki |
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson |
| 2003/0186251 A1 | 10/2003 | Dunn et al. |
| 2003/0207296 A1 | 11/2003 | Park et al. |
| 2003/0207300 A1 | 11/2003 | Matray et al. |
| 2004/0047769 A1 | 3/2004 | Tanaami |
| 2004/0091864 A1 | 5/2004 | French et al. |
| 2004/0096368 A1 | 5/2004 | Davis et al. |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0147435 A1 | 7/2004 | Hawiger et al. |
| 2004/0157243 A1 | 8/2004 | Huang et al. |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan et al. |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0057634 A1 | 3/2006 | Rye |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0281092 A1 | 12/2006 | Wille et al. |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison et al. |
| 2007/0117134 A1 | 5/2007 | Kou |
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2007/0281317 A1 | 12/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson Svahn et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0220385 A1 | 9/2009 | Brown et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal et al. |
| 2009/0298709 A1 | 12/2009 | Ma |
| 2009/0311694 A1 | 12/2009 | Gallagher et al. |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |

(56) References Cited

U.S. PATENT DOCUMENTS

| | | |
|---|---|---|
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0017654 A1 | 1/2015 | Gorfinkel et al. |
| 2015/0066385 A1 | 3/2015 | Schnall-levin et al. |
| 2015/0072867 A1 | 3/2015 | Soldatov et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Iafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0010151 A1 | 1/2016 | Fan et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0253584 A1 | 9/2016 | Fodor et al. |
| 2016/0257993 A1 | 9/2016 | Fu et al. |
| 2016/0258012 A2 | 9/2016 | Fodor et al. |
| 2016/0265027 A1 | 9/2016 | Sanches-Kuiper et al. |
| 2016/0265069 A1 | 9/2016 | Fan et al. |
| 2016/0289669 A1 | 10/2016 | Fan et al. |
| 2016/0289670 A1 | 10/2016 | Samuels et al. |
| 2016/0289740 A1 | 10/2016 | Fu et al. |
| 2016/0298180 A1 | 10/2016 | Chee |
| 2016/0312276 A1 | 10/2016 | Fu et al. |
| 2016/0320720 A1 | 11/2016 | Murata et al. |
| 2016/0326584 A1 | 11/2016 | Fodor et al. |
| 2016/0355879 A1 | 12/2016 | Kamberov et al. |

(56) References Cited

U.S. PATENT DOCUMENTS

| | | |
|---|---|---|
| 2016/0376583 A1 | 12/2016 | Fodor et al. |
| 2016/0376648 A1 | 12/2016 | Fodor et al. |
| 2017/0044525 A1 | 2/2017 | Kaper et al. |
| 2017/0073730 A1 | 3/2017 | Betts et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0337459 A1 | 11/2017 | Fodor et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0002764 A1 | 1/2018 | Fan et al. |
| 2018/0016634 A1 | 1/2018 | Hindson et al. |
| 2018/0024139 A1 | 1/2018 | Peikon et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0251825 A1 | 9/2018 | Stoeckius et al. |
| 2018/0258482 A1 | 9/2018 | Hindson et al. |
| 2018/0258500 A1 | 9/2018 | Fan et al. |
| 2018/0267036 A1 | 9/2018 | Fan et al. |
| 2018/0276332 A1 | 9/2018 | Fan et al. |
| 2018/0282803 A1 | 10/2018 | Belgrader et al. |
| 2018/0291470 A1 | 10/2018 | Fan et al. |
| 2018/0002738 A1 | 11/2018 | Wang et al. |
| 2018/0320241 A1 | 11/2018 | Nolan et al. |
| 2018/0327835 A1 | 11/2018 | Fodor et al. |
| 2018/0327836 A1 | 11/2018 | Fodor et al. |
| 2018/0327866 A1 | 11/2018 | Fan et al. |
| 2018/0327867 A1 | 11/2018 | Fan et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0025304 A1 | 1/2019 | Vigneault et al. |
| 2019/0032129 A1 | 1/2019 | Hindson et al. |
| 2019/0040474 A1 | 2/2019 | Fan et al. |
| 2019/0085412 A1 | 3/2019 | Fan et al. |
| 2019/0095578 A1 | 3/2019 | Shum et al. |
| 2019/0100798 A1 | 4/2019 | Fodor et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0161743 A1 | 5/2019 | Church et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |
| 2019/0203291 A1 | 7/2019 | Hindson et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338278 A1 | 11/2019 | Shum et al. |
| 2019/0338357 A1 | 11/2019 | Fan et al. |
| 2020/0109437 A1 | 4/2020 | Chang et al. |
| 2020/0124601 A1 | 4/2020 | Fan et al. |
| 2020/0149037 A1 | 5/2020 | Shum |
| 2021/0198754 A1 | 7/2021 | Fan et al. |
| 2021/0214770 A1 | 7/2021 | Prosen et al. |
| 2021/0214784 A1 | 7/2021 | Prosen et al. |
| 2021/0222244 A1 | 7/2021 | Martin et al. |
| 2021/0230582 A1 | 7/2021 | Fu et al. |
| 2021/0230583 A1 | 7/2021 | Lam et al. |
| 2021/0230666 A1 | 7/2021 | Wu et al. |
| 2021/0246492 A1 | 8/2021 | Song et al. |
| 2021/0263019 A1 | 8/2021 | Martin et al. |

FOREIGN PATENT DOCUMENTS

| | | |
|---|---|---|
| EP | 1473080 | 11/2004 |
| EP | 1647600 | 4/2006 |
| EP | 1845160 | 10/2007 |
| EP | 2036989 | 3/2009 |
| EP | 1379693 | 5/2009 |
| EP | 2204456 | 7/2010 |
| EP | 2431465 | 3/2012 |
| EP | 2203749 | 8/2012 |
| EP | 2511708 | 10/2012 |
| EP | 2538220 | 12/2012 |
| EP | 2623613 | 8/2013 |
| EP | 2702146 | 3/2014 |
| EP | 1745155 | 10/2014 |
| EP | 2805769 | 11/2014 |
| EP | 2556171 | 9/2015 |
| EP | 2989215 | 3/2016 |
| EP | 2970958 | 12/2017 |
| EP | 3263715 | 1/2018 |
| EP | 3286326 | 2/2018 |
| EP | 3136103 | 8/2018 |
| EP | 2954102 | 12/2018 |
| EP | 3428290 | 1/2019 |
| EP | 2970957 | 4/2019 |
| EP | 3058092 | 5/2019 |
| EP | 3256606 | 5/2019 |
| EP | 3327123 | 8/2019 |
| GB | 2293238 A | 3/1996 |
| JP | H04108385 | 4/1992 |
| JP | 2001078768 | 3/2001 |
| JP | 2005233974 | 9/2005 |
| JP | 2007504831 | 3/2007 |
| JP | 2008256428 | 10/2008 |
| JP | 2013039275 | 2/2013 |
| WO | WO1989001050 | 2/1989 |
| WO | WO1996024061 | 8/1996 |
| WO | WO1997010365 | 3/1997 |
| WO | WO1999015702 | 4/1999 |
| WO | WO1999028505 | 6/1999 |
| WO | WO2000058516 | 10/2000 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003035829 | 5/2003 |
| WO | WO2004017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |

(56) References Cited

FOREIGN PATENT DOCUMENTS

| | | |
|---|---|---|
| WO | WO2005111243 | 11/2005 |
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010059820 | 5/2010 |
| WO | WO2010117620 | 10/2010 |
| WO | WO2010131645 | 11/2010 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 2/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015168161 | 11/2015 |
| WO | WO2015179339 | 11/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016130578 | 8/2016 |
| WO | WO2016160965 | 8/2016 |
| WO | WO2016138496 | 9/2016 |
| WO | WO2016138500 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018174827 | 9/2018 |
| WO | WO2018217862 | 11/2018 |
| WO | WO2018218222 | 11/2018 |
| WO | WO2018222548 | 12/2018 |
| WO | WO2018226293 | 12/2018 |
| WO | WO2019055852 | 3/2019 |
| WO | WO2019076768 | 4/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2013137737 | 9/2019 |
| WO | WO2019178164 | 9/2019 |
| WO | WO2019213237 | 11/2019 |
| WO | WO2019213294 | 11/2019 |
| WO | WO2020028266 | 2/2020 |

(56) References Cited

FOREIGN PATENT DOCUMENTS

| | | |
|---|---|---|
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020154247 | 7/2020 |
| WO | WO2020167920 | 8/2020 |
| WO | WO2020214642 | 10/2020 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |

OTHER PUBLICATIONS

Advisory Action dated Aug. 25, 2020 in U.S. Appl. No. 15/084,307.
Biosciences Product Catalogue, Dynal® Catalog 1999, Oslo, Norway, 49-51.
Examination Report dated Jul. 6, 2020 in European Patent Application No. 17781265.8.
Examination Report dated Sep. 21, 2020 in European Patent Application No. 18703156.2.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
International Search Report and Written Opinion dated May 18, 2020 in PCT Application No. PCT/US2020/014339.
International Search Report and Written Opinion dated Jun. 30, 2020 in PCT Application No. PCT/US2020/017890.
Kooiker & Xue, "cDNA Library Preparation," Cereal Genomics 2013, 1099, 29-40.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Rhee et al., "Simultaneous detection of mRNA and protein stem cell markers in live cells," BMC Biotechnology 2009, 9(30), 1-10.
Search Report and Written Opinion dated Aug. 26, 2020 in Singapore Patent Application No. 10201806890V.
S.H.Ko, "An 'equalized cDNA library' by the reassociation of short double-stranded cDNAs," Nucleic Acids Res. 1990, 18(19), 5705-5711.
10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://www.thescientist.com/features/2018-top-10-innovations-65140, 16 pp.
Achim et al., "High-throughput spatial mapping of single-cell RNA-seq data to tissue of origin," Nature Biotechnology 2015, 33(5), 503-511.
Advisory Action dated Nov. 29, 2019 in U.S. Appl. No. 15/084,307.
Advisory Action dated Dec. 2, 2019 in U.S. Appl. No. 15/055,407.
Agasti et al., "Photocleavable DNA barcode-antibody conjugates allow sensitive and multiplexed protein analysis in single cell," J Am Chem Soc. 2012, 134(45), 18499-18502.
Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLiD™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-Cell Mass Cytometry of Differential Immune and Drug Responses Across a Human Hematopoietic Continuum," Science 2011, 332(6030), 687-696.
Bionumbers, "Useful fundamental numbers in molecular biology," http://bionumbers.hms.harvard.edu/KeyNumbers/aspx, 1-4.
Bioscribe "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. 1996, 6, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.

(56) References Cited

OTHER PUBLICATIONS

Brodin et al., "Challenges with Using Primer IDs to Improve Accuracy of Next Generation Sequencing," PLoS One 2015, 19(3), 1-12.

Buggenum et al., "A covalent and cleavable antibody DNA conjugation strategy for sensitive protein detection via immunoPCR," Scientific Reports 2016, 6(22675), 1-12.

Buschmann et al., Enhancing the detection of barcoded reads in high throughput DNA sequencing DNA by controlling the false discovery rate, BMC Bioinformatics, 15(1), 264, 1-16.

Bustin, "Absolute quantification of mRNA using real-time reverse transcription polymerase chain reaction assays," Journal of Molecular Endocrinology 2000, 25, 169-193.

Butkus, "Cellular research set to launch first gene expression platform using 'molecular indexing' technology," GenomeWeb 2014, 1-5.

Cai, "Turning single cells in microarrays by super-resolution barcoding," Briefings in Functional Genomics 2012, 12(2), 75-80.

Cao et al., "Comprehensive single-cell transcriptional profiling of a multicellular organism," Science 2017, 357, 661-667.

Carr et al., "Inferring relative proportions of DNA variants from sequencing electropherograms," Bioinformatics 2009, 25(24), 3244-3250.

Caruccio et al., "Nextera (TM) Technology for NGS DNA Library Preparation: Simultaneous Fragmentation and Tagging by in Vitro Transposition," EpiBio 2009, 16(3), 4-6.

Casbon et al., "A method for counting PCR template molecules with application to next-generation sequencing," Nucleic Acids Res. 2011, 39(12), e81, 1-8.

Castellarnau et al., "Stochastic particle barcoding for single-cell tracking and multiparametric analysis," Small 2015, 11(4), 489-498.

Castle et al., "DNA copy number, including telomeres and mitochondria, assayed using next-generation sequencing," BMC Genomics 2010, 11(244), 1-11.

Chamberlain et al., "Deletion screening of the Duchenne muscular dystrophy locus via multiplex DNA amplification," Nucleic Acids Res. 1988, 16(23), 11141-11156.

Chang et al., "Detection of Allelic Imbalance in Ascitic Supernatant by Digital Single Nucleotide Polymorphism Analysis," Clinical Cancer Research, 8, 2580-2585.

Chapin et al., "Rapid microRNA Profiling on Encoded Gel Microparticles," Angew Chem Int Ed Engl. 2011, 50(10), 2289-2293.

Chee et al., "Accessing genetic information with high-density DNA arrays," Science 1996, 274, 610-614.

Chee, "Enzymatic multiplex DNA sequencing," Nucleic Acids Research 1991, 19(12), 3301-3305.

Chen et al., "Spatially resolved, highly multiplexed RNA profiling in single cells," Science Express 2015, 348(6233), aaa6090, 1-36.

Church et al., "Multiplex DNA sequencing," Science 1988, 240(4849), 185-188.

Civil Cover Sheet filed Nov. 15, 2018 in the USDC for the District of Delaware, C.A. 18-1800-RGA, 1 pp.

Clontech Laboratories, Inc., "SMART™ PCR cDNA Synthesis Kit User Manual," Clontech 2007, 1-39.

Cloonan et al., "Stem cell transcriptome profiling via massive-scale mRNA sequencing", Nature Methods 2008, 5(7), 613-619.

Combined Search and Examination Report dated Aug. 6, 2014 in UK Patent Application No. 1408829.8.

Combined Search and Examination Report dated Feb. 21, 2017 in UK Patent Application No. 1609740.4.

Communication of a Notice of Opposition dated Jul. 21, 2016 in European Patent Application No. EP 10762102.1.

Complaint filed in Becton, *Dickinson and Company* and *Cellular Research Inc.* v.*10X Genomics, Inc.* dated Nov. 15, 2018 in the USDC for the District of Delaware, C.A. 18-1800-RGA, 141 pp.

Costa et al., "Single-Tube Nested Real-Time PCR as a New Highly Sensitive Approach to Trace Hazelnut," Journal of Agricultural and Food Chemistry 2012, 60, 8103-8110.

Costello et al., "Discovery and characterization of artefactual mutations in deep coverage targeted capture sequencing data due to oxidative DNA damage during sample preparation," Nucleic Acids Res 2013, 41(6), e67, 1-12.

Cotten et al., "Selection of proteins with desired properties from natural proteome libraries using mRNA display," Nature Protocols 2011, 6, 1163-1182.

Cox, "Bar coding objects with DNA," Analyst 2001, 126, 545-547.

Craig et al., "Identification of genetic variants using bar-coded multiplexed sequencing," Nat Methods 2008, 5(10), 887-893.

Cusanovich et al., "Multiplex single-cell profiling of chromatin accessibility by combinatorial cellular indexing," Science 2015, 348(6237), 910-914.

Custom Antibody Services, Precision Antibody, accessed Apr. 16, 2014, 2 pp.

Daines et al., "High-throughput multiplex sequencing to discover copy number variants in *Drosophila*," Genetics 2009, 182(4), 182, 935-941.

Dalerba et al., "Single-cell dissection of transcriptional heterogeneity in human colon tumors," Nat Biotechnol. 2011, 29(12), 1120-1127.

D'Antoni et al., "Rapid quantitative analysis using a single molecule counting approach," Anal Biochem. 2006, 352, 97-109.

Daser et al., "Interrogation of genomes by molecular copy-number counting (MCC)," Nature Methods 2006, 3(6), 447-453.

Day et al., "Immobilization of polynucleotides on magnetic particles," Biochem. J. 1991, 278, 735-740.

Decision of Refusal dated Aug. 21, 2017 in Japanese Patent Application No. 2014-558975.

Defendant *10X Genomics, Inc.*'s Letter to Judge Andrews in Response to Plaintiff's Letter of Supplemental Authority, dated Jul. 11, 2019 in the USDC for the District of Delaware, C.A. 18-1800-RGA, 2 pp.

Defendant *10X Genomic*'s Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.

Defendant *10X Genomics, Inc.*'s Motion for Admission Pro Hac Vice Pursuant to Local Rule 83.5, dated Jan. 18, 2019 in the USDC District of Delaware, C.A. No. 18-1800-RGA, 5 pp.

Defendant *10X Genomics, Inc.*'s Motion to Dismiss Pursuant to Federal Rule of Civil Procedure 12(b)(6), dated Jan. 18, 2019 in the USDC for the District of Delaware, C.A. 18-1800-RGA, 1 pp.

Defendant *10X Genomics, Inc.*'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.

Defendant *10X Genomic*'s Notice of Service for Initial Disclosures served to Opposing Counsel, dated Jun. 7, 2019 in the USDC for the District of Delaware, C.A. 18-1800-RGA, 2 pp.

Defendant *10X Genomic Inc.*'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.

Defendant *10X Genomics Inc*'s, Notice of Service of Technical Documents, dated Jul. 8, 2019 in the USDC for the District of Delaware, C.A. 18-1800-RGA, 2 pp.

Defendant *10X Genomics, Inc.*'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.

Defendant *10X Genomics, Inc.*'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.

Defendant *10X Genomics, Inc.*'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.

Defendant *10X Genomics, Inc*'s Proposed Order for Dismissal pursuant to Federal Rules of Civil Procedure 12(b)(6), filed Mar. 1, 2019 in the USDC for the District of Delaware, C.A. 18-1800-RGA, 1 pp.

(56) References Cited

OTHER PUBLICATIONS

Defendant *10X Genomic*'s Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant *10X Genomic*'s Request for Oral Argument Under D. Del. LR 7.1.4, dated Apr. 18, 2019 in the USDC for the District of Delaware, C.A. 18-1800-RGA 2 pp.
Defendant *10X Genomic*'s Response Letter to Judge Richard G. Andrews re Request for a Rule 16, dated Apr. 16, 2019 in the USDC for the District of Delaware, C.A. 18-1800-RGA, 2 pp.
Defendant *10X Genomics, Inc.*'s Rule 7.1 Disclosure Statement, dated Jan. 18, 2019 in the USDC District of Delaware, C.A. No. 18-1800-RGA, 1 pp. 1.
Delley et al., "Combined aptamer and transcriptome sequencing of single cells," bioRxiv 2017, 1-10.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.

(56) References Cited

OTHER PUBLICATIONS

Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.

Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Mar. 26, 2019 in PCT Application No. PCT/US2017/053331.
International Preliminary Report on Patentability dated Aug. 15, 2019 in PCT Application No. PCT/US2018/014385.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.

(56) References Cited

OTHER PUBLICATIONS

International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Fees dated May 7, 2020 in PCT Application No. PCT/US2020/017890.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from a retroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Junker et al., "Single-Cell Transcriptomics Enters the Age of Mass Production," Molecular Cell 2015, 58, 563-564.

Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute numbers of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., VarScan: variant detection in massively parallel sequencing of individual and pooled samples, Bioinformatics 2009, 25(17), 2283-2285.
Kolodziejczyk et al., The Technology and Biology of Single-Cell RNA Sequencing, Molecular Cell 2015, 58, 610-620.
Konig et al., iCLIP reveals the function of hnRNAP particles in splicing at individual nucleotide resolution, Nature Structural & Molecular Biology 2010, 17(7), 909-916.
Kotake et al., "A simple nested RT-PCR method for quantitation of the relative amounts of multiple cytokine mRNAs in small tissue samples," Journal of Immunological Methods 1996, 199, 193-203.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lamble et al., "Improved workflows for high throughput library preparation using the transposome-based nextera system," BMC Biotechnology 2013, 13, 104, 1-10.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide," Anal Chem. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.
Lee et al., "Highly Multiplexed Subcellular RNA Sequencing in Situ," Science 2014, 343, 1360-1363.

(56) References Cited

OTHER PUBLICATIONS

Lee et al., "Universal process-inert encoding architecture for polymer microparticles," Nature Materials 2014, 13(5), 524-529.
Letter regarding the opposition procedure dated Jul. 22, 2015 for European Patent Application No. 11810645.9.
Letter to Judge Richard G. Andrews Requesting a Rule 16 Conference, dated Apr. 15, 2019 in the USDC for the District of Delaware, C.A. 18-1800 (RGA), 1 pp.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Lin et al., "Self-Assembled Combinatorial Encoding Nanoarrays for Multiplexed Biosensin," Nano Lett. 2007, 7(2), 507-512.
Liu et al., "Single-cell transcriptome sequencing: recent advances and remaining challenges," F1000Research 2016, 5(F1000 Faculty Rev)(182), 1-9.
Lizardi et al., "Mutation detection and single-molecule counting using isothermal rolling-circle amplification," Nat Genet. 1998, 19, 225-232.
Lockhart et al., "Expression monitoring by hybridization to high-density oligonucleotide arrays," Nature Biotechnology 1996, 14, 1675-1680.
Lovatt et al., "Transcriptome in vivo analysis (TIVA) of spatially defined single cells in live tissue," Nat Methods 2014, 11(2), 190-196.
Loy et al., "A rapid library preparation method with custom assay designs for detection of variants at 0.1% allelic frequency in liquid biopsy samples," Oct. 2, 2018, 1 p.
Lucito et al., "Representational Oligonucleotide Microarray Analysis: A High-Resolution Method to Detect Genome Copy Number Variation," Genome Research 2003, 13, 2291-2305.
Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Maamar et al., "Noise in Gene Expression Determines Cell Fate in Bacillus subtilis," Science 2007, 317, 526-529.
Macaulay et al., "Single Cell Genomics: Advances and Future Perspectives," PLoS Genetics 2014, 10(1), 1-9.
Macaulay et al., "G&T-seq: parallel sequencing of single-cell genomes and transcriptomes," Nature Methods 2015, 1-7.
Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," BioTechniques 2008, 45(1), 95-97.
Makrigiorgos et al., "A PCR-Based amplification method retaining quantities difference between two complex genomes," Nature Biotech 2002, 20(9), 936-939.
Marcus et al., 2006, "Microfluidic single-cell mRNA isolation and analysis," Anal Chem. 2006, 78, 3084-3089.
Mardis, "Next-generation DNA sequencing methods", Annu. Rev. Genomics Hum. Genet. 2008, 9, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.
Martinez et al., "A microfluidic approach to encapsulate living cells in uniform alginate hydrogel microparticles," Macromol. Biosci 2012, 12, 946-951.
Massachusetts General Hospital, Overview of Illumina Chemistry, http://nextgen.mgh.harvard.edu/IlluminaChemistry.html, downloaded Jan. 28, 2020, 2 pp.
McCloskey et al., "Encoding PCR products with batch-stamps and barcodes," Biochem Genet. 2007, 45(11-12), 761-767.
Medvedev et al., "Detecting copy number variation with mated short reads," Genome Res. 2010, 20, 1613-1622.
Mei et al., "Identification of recurrent regions of Copy-Number Variants across multiple individuals," BMC Bioinformatics 2010, 11, 147, 1-14.
Merriam-Webster, definition of associate: http://www.merriam-webster.com/dictionary/associate, accessed Apr. 5, 2016.
Meyer et al., "Parallel tagged sequencing on the 454 platform," Nature Protocols 2008, 3(2), 267-278.
Miller et al., Directed evolution by in vitro compartmentalization, Nature Methods 2006, 3(7), 561-570.
Miner et al., "Molecular barcodes detect redundancy and contamination in hairpin-bisulfite PCR," Nucleic Acids Research 2004, 32(17), e135, 1-4.
Mortazavi et al., "Mapping and quantifying mammalian transcriptomes by RNA-Seq," Nat. Methods 2008, 5(7), 621-628.
Motion and Order for Admission Pro Hac Vice Pursuant to Local Rule 83.5, dated Jan. 24, 2019 in the USDC District of Delaware, C.A. No. 18-1800-RGA, 7 pp.
Nadai et al., Protocol for nearly full-length sequencing of HIV-1 RNA from plasma, PLoS One 2008, 3(1), e1420, 1-6.
Nagai et al., "Development of a microchamber array for picoleter PCR," Anal. Chem. 2001, 73, 1043-1047.
Navin et al., "The first five years of single-cell cancer genomics and beyond," Genome Research 2015, 25, 1499-1507.
Newell et al., Cytometry by time-of-flight shows combinatorial cytokine expression and virus-specific cell niches within a continuum of CD8+ T cell phenotypes. Immunity 2012, 36(1), 142-152.
Non-Final Office Action dated Oct. 3, 2013 in U.S. Appl. No. 12/969,581.
Non-Final Office Action dated Feb. 18, 2015 for U.S. Appl. No. 14/540,007.
Non-Final Office Action dated Feb. 26, 2015 for U.S. Appl. No. 14/540,029.
Non-Final Office Action dated Mar. 19, 2015 in U.S. Appl. No. 14/540,018.
Non-Final Office Action dated May 7, 2015 for U.S. Appl. No. 13/327,526.
Non-Final Office Action dated Dec. 3, 2015 for U.S. Appl. No. 14/281,706.
Non-Final Office Action dated Dec. 31, 2015 for U.S. Appl. No. 14/800,526.
Non-Final Office Action dated Apr. 11, 2016 in U.S. Appl. No. 14/472,363.
Non-Final Office Action dated May 10, 2016 in U.S. Appl. No. 14/381,488.
Non-Final Office Action dated May 13, 2016 in U.S. Appl. No. 14/508,911.
Non-Final Office Action dated Aug. 17, 2016 for U.S. Appl. No. 14/800,526.
Non-Final Office Action dated Sep. 26, 2016 in U.S. Appl. No. 15/167,807.
Non-Final Office Action dated Oct. 11, 2016 in U.S. Appl. No. 15/224,460.
Non-Final Office Action dated Jan. 19, 2017 in U.S. Appl. No. 15/055,445.
Non-Final Office Action dated Mar. 24, 2017 in U.S. Appl. No. 15/409,355.
Non-Final Office Action dated Jun. 2, 2017 in U.S. Appl. No. 14/381,526.
Non-Final Office Action dated Jun. 7, 2017 in U.S. Appl. No. 14/381,488.
Non-Final Office Action dated Jul. 28, 2017 in U.S. Appl. No. 14/975,441.
Non-Final Office Action dated Sep. 8, 2017 in U.S. Appl. No. 15/046,225.
Non-Final Office Action dated Sep. 8, 2017 in U.S. Appl. No. 15/134,967.
Non-Final Office Action dated Nov. 1, 2017 in U.S. Appl. No. 15/667,125.
Non-Final Office Action dated Nov. 9, 2017 in U.S. Appl. No. 15/004,618.

(56) References Cited

OTHER PUBLICATIONS

Non-Final Office Action dated Jan. 9, 2018 in U.S. Appl. No. 15/217,896.
Non-Final Office Action dated Jan. 12, 2018 in U.S. Appl. No. 15/217,886.
Non-Final Office Action dated Mar. 8, 2018 in U.S. Appl. No. 15/608,780.
Non-Final Office Action dated Apr. 6, 2018 in U.S. Appl. No. 15/603,239.
Non-Final Office Action dated Jul. 25, 2018 in U.S. Appl. No. 15/108,268.
Non-Final Office Action dated Oct. 4, 2018 in U.S. Appl. No. 15/260,106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant *10X Genomics, Inc.*, dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.

(56) References Cited

OTHER PUBLICATIONS

Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.
Ozkumur et al., "Inertial Focusing for Tumor Antigen-Dependent and—Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Pérez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes and sample integrity: BestKeeper—Excel-based tool using pair-wise correlations," Biotechnology Letters, 26(6), 505-515.
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics 2005, 6, 331-354.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible by microfluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.

Qiu et al., "DNA Sequence-Based "Bar Codes" for Tracking the Origins of Expressed Sequence Tags from a Maize cDNA Library Constructed Using Multiple mRNA Sources," Plant Physiol. 2003, 133, 475-481.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody-DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
Shoemaker et al., "Quantitative phenotypic analysis of yeast deletion mutants using a highly parallel molecular bar-coding strategy," Nature Genetics 1996, 14, 450-456.

(56) References Cited

OTHER PUBLICATIONS

Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019,1129, 63-79.
Simpson et al., "Copy number variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant *10X Genomics, Inc.* filed Nov. 16, 2018 in the USDC for the District of Delaware, Civil Action No. 18-1800, 2 pp.
Sun et al., "Ultra-deep profiling of alternatively spliced *Drosophila dscam* isoforms by circularization-assisted multi-segment sequencing," EMBO J. 2013, 32(14), 2029-2038.
Takahashi et al., "Novel technique of quantitative nested real-time PCR assay for *Mycobacterium tuberculosis* DNA," Journal of Clinical Microbiology 2006, 44, 1029-1039.
Tan et al., "Genome-wide comparison of DNA hydroxymethylation in mouse embryonic stem cells and neural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation of the highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.

Tomaz et al., "Differential methylation as a cause of allele dropout at the imprinted GNAS locus," Genet Test Mol Biomarkers 2010, 14(4), 455-460.
Treutlein et al., Reconstructing lineage hierarchies of the distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization of the Yeast Transcriptome," Cell 1997, 88, 243-251.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21(9), 1529-1542.
Ye et al., Fluorescent microsphere-based readout technology for multiplexed human single nucleotide polymorphism analysis and bacterial identification, Human Mutation 2001, 17(4), 305-316.

(56) References Cited

OTHER PUBLICATIONS

Yoon et al., Sensitive and accurate detection of copy number variants using read depth of coverage, Genome Res. 2009, 19, 1586-1592.
Zagordi et al., "Error correction of next-generation sequencing data and reliable estimation of HIV quasispecies," Nucleic Acids Research 2010, 38(21), 7400-7409.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung Carcinomas Revealed by Single Nucleotide Polymorphism Array Analysis," Cancer Research 2005, 65(13), 5561-5570.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by Maldi-Tof MS," Mol. BioSyst. 2012, 8, 2395-2404.
Zhu et al., "Reverse Transcriptase Template Switching: A SMART Approach for Full-Length cDNA Library Construction," BioTechniques 2001, 30(4), 892-897.
Examination Report dated Nov. 12, 2020 in European Patent Application No. 18716877.8.
Examination Report dated Dec. 3, 2020 in European Patent Application No. 16719706.0.
Examination Report dated Mar. 25, 2021 in European Patent Application No. 17781265.8.
Final Office Action dated Dec. 7, 2020 in U.S. Appl. No. 16/012,584.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
International Preliminary Report on Patentability dated Nov. 3, 2020 in PCT Application No. PCT/US2019/030175.
International Preliminary Report on Patentability dated Nov. 3, 2020 in PCT Application No. PCT/US2019/030245.
International Preliminary Report on Patentability dated Feb. 9, 2021 in PCT Application No. PCT/US2019/043949.
International Preliminary Report on Patentability dated Feb. 23, 2021 in PCT Application No. PCT/US2019/046549.
International Preliminary Report on Patentability dated Mar. 2, 2021 in PCT Application No. PCT/US2019/048179.
International Search Report and Written Opinion dated Nov. 12, 2020 in PCT Application No. PCT/US2020/042880.
International Search Report and Written Opinion dated Jan. 19, 2021 in PCT Application No. PCT/US2020/059419.
New COVID-19 Variants, Centers for Disease Control and Prevention 2021, accessed Jan. 21, 2021, 3 pp.
Non-Final Office Action dated Dec. 4, 2020 in U.S. Appl. No. 16/677,012.
Non-Final Office Action dated Dec. 9, 2020 in U.S. Appl. No. 16/788,743.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Notice of Allowance dated Sep. 23, 2020 in Korean Patent Application No. 10-2016-7008144.
Notice of Allowance dated Oct. 29, 2020 in U.S. Appl. No. 15/987,851.
Notice of Allowance dated Jan. 13, 2021 in U.S. Appl. No. 14/381,488.
Notice of Allowance dated Jan. 13, 2021 in U.S. Appl. No. 15/459,977.
Office Action dated Oct. 29, 2020 in Chinese Patent Application No. 2018800377201.
Office Action dated Jan. 4, 2021 in Japanese Patent Application No. 2017-549390.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Stoeckius et al., "Cell Hashing with barcoded antibodies enables multiplexing and doublet detection for single cell genomics," Genome Biology 2018, 19(224), 1-12.
Summons to Attend Oral Proceedings dated Nov. 16, 2020 in European Patent Application No. 17202409.3.
TotalSeq™-A0251 anti-human Hashtag 1 Antibody, BioLegend®, Jul. 2018, 1-10.
Zeberg et al., "The major genetic risk factor for severe COVID-19 is inherited from Neanderthals," Nature 2020, 587(7835), 1-13.
Adey et al., "Rapid, low-input, low-bias construction of shotgun fragment libraries by high-density in vitro transposition," Genome Biology 2010, 11(R19), in 17 pages.
Ahern, "Biochemical, Reagent Kits Offer Scientists Good Return on Investment," The Scientist 1995, 9(15), in 5 pages.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Examination Report dated Oct. 8, 2021 in European Patent Application No. 18716877.8.
Extended European Search Report dated May 6, 2021 in European Patent Application No. 20207621.2.
Extended European Search Report dated May 28, 2021 in European Patent Application No. 20209777.0.
Final Office Action dated Jun. 15, 2021 in U.S. Appl. No. 15/084,307.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Fitzgerald and Grivel, "A Universal Nanoparticle Cell Secretion Capture Assay," Cytometry Part A 2012, 83A(2), 205-211.
GenBank Accession No. NM_000518.5 for *Homo sapiens* hemoglobin subunit beta (HBB), mRNA. Mar. 22, 2021 [online], [retrieved on Apr. 27, 2021], retrieved from the Internet: <URL: www.ncbi.nlm.nih.gov/nuccore/NM_000518.5?report=Genbank (Year: 2021).
Gertz et al., "Transposase mediated construction of RNA-seq libraries," Genome Research 2012, 22, 134-141.
Gratton et al., "Cell-permeable peptides improve cellular uptake and therapeutic gene delivery of replication-deficient viruses in cells and in vivo," Nature Medicine 2003, 9(3), 357-362.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
International Search Report and Written Opinion dated May 4, 2021 in PCT Application No. PCT/US2021/013109.

(56) References Cited

OTHER PUBLICATIONS

International Search Report and Written Opinion dated May 11, 2021 in PCT Application No. PCT/US2021/013748.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
Invitation to Pay Fees dated May 25, 2021 in PCT Application No. PCT/US2021/01598.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Janeway et al., "Structural variation in immunoglobulin constant regions," Immunology: The Immune System in Health and Disease 1999, 101-103.
Lan et al., "Droplet barcoding for massively parallel single-molecule deep sequencing," Nature Communications 2016, 7(11784), in 10 pages.
Livingstone, "rRNA depletion, poly(A) enrichment, or exonuclease treatment?" Tebu-Bio Blog 2015, in 1 page.
Mair et al., "A Targeted Multi-omic Analysis Approach Measures Protein Expression and Low-Abundance Transcripts on the Single-Cell Level", Cell Reports 2020, 31(1), 107499, in 20 pages.
Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Notice of Allowance dated Apr. 26, 2021 in Japanese Patent Application No. 2019-014564.
Notice of Allowance dated Jun. 10, 2021 in Chinese Patent Application No. 2018800377201.
Notice of Allowance dated Aug. 16, 2021 in Japanese Patent Application No. 2018-512152.
Notice of Allowance dated Sep. 10, 2021 in U.S. Appl. No. 16/535,080.
Novus Biologicals, "Fixation and Permeability in ICC IF," Novus Biologicals 2021, 1-3.
Office Action dated May 10, 2021 in Japanese Patent Application No. 2019-566787.
Office Action dated May 21, 2021 in Chinese Patent Application No. 201680007351.2.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.
Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021, in Korean Patent Application No. 10-2019-7038794.
Office Action dated Sep. 14, 2021, in Chinese Patent Application No. 2016800523302.
O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Restriction Requirement dated May 5, 2021 in U.S. Appl. No. 16/400,886.
Restriction Requirement dated May 28, 2021 in U.S. Appl. No. 16/781,814.
Restriction Requirement dated Jun. 4, 2021 in U.S. Appl. No. 16/551,620.
Restriction Requirement dated Sep. 20, 2021 in U.S. Appl. No. 16/525,054.
Restriction Requirement dated Oct. 1, 2021 in U.S. Appl. No. 16/525,054.
Schouten et al., "Relative quantification of 40 nucleic acid sequences by multiplex ligation-dependent probe amplification," Nucleic Acids Research 2002, 30(12), e57.
Shapiro et al., "Single-cell sequencing-based technologies will revolutionize whole-organism science," Nature Reviews Genetics 2013, 14, 618-629.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Takara Bio, "SMARTer Human BCR IgG IgM H/K/L Profiling Kit User Manual," Takara Bio USA Inc. 2019, 1-22.
Trzupek et al., "Discovery of CD80 and CD86 as recent activation markers on regulatory T cells by protein-RNA single-cell analysis", Genome Medicine 2020, 12(1), in 22 pages.
Vestheim et al., "Application of Blocking Oligonucleotides to Improve Signal-to-Noise Ratio in a PCR," Methods in Molecular Biology 2011, 687, 265-274.
Wang et al., "Tagmentation-based whole-genome bisulfite sequencing," Nature Protocols 2013, 8(10), 2022-2032.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.

* cited by examiner

SEQUENCE LISTING

```
<160> NUMBER OF SEQ ID NOS: 4

<210> SEQ ID NO 1
<211> LENGTH: 90
<212> TYPE: DNA
<213> ORGANISM: Artificial Sequence
<220> FEATURE:
<223> OTHER INFORMATION: Exemplary oligonucleotide
<220> FEATURE:
<221> NAME/KEY: misc_feature
<222> LOCATION: (1)..(1)
<223> OTHER INFORMATION: V = A, G or C
<220> FEATURE:
<221> NAME/KEY: misc_feature
<222> LOCATION: (37)..(44)
<223> OTHER INFORMATION: n = sequence for the sample label, n can be a
      or t or c or g
<220> FEATURE:
<221> NAME/KEY: misc_feature
<222> LOCATION: (45)..(52)
<223> OTHER INFORMATION: n = sequence for the molecular label, n can be
      a or t or c or g
<220> FEATURE:
```

```
<221> NAME/KEY: misc_feature
<222> LOCATION: (53)..(60)
<223> OTHER INFORMATION: CGCTAGCG = an AsiSI restriction site

<400> SEQUENCE: 1 vtttttttttt ttttttttg ctgcgagaag gctagannnn nnnnnnnnnn nncgctagcg     60
gttacaggag gtctggagga cattggcgat                                      90

<210> SEQ ID NO 2
<211> LENGTH: 90
<212> TYPE: DNA
<213> ORGANISM: Artificial Sequence
<220> FEATURE:
<223> OTHER INFORMATION: Exemplary oligonucleotide
<220> FEATURE:
<221> NAME/KEY: misc_feature
<222> LOCATION: (37)..(44)
<223> OTHER INFORMATION: n = sequence for the sample label, n can be a
      or t or c or g
<220> FEATURE:
<221> NAME/KEY: misc_feature
<222> LOCATION: (45)..(52)
<223> OTHER INFORMATION: n = sequence for the molecular label, n can be
      a or t or c or g
<220> FEATURE:
<221> NAME/KEY: misc_feature
<222> LOCATION: (53)..(60)
<223> OTHER INFORMATION: CGCTAGCG = an AsiSI restriction site

<400> SEQUENCE: 2 ttttttttttt ttttttttg ctgcgagaag gctagannnn nnnnnnnnnn nncgctagcg     60
gttacaggag gtctggagga cattggcgat                                      90

<210> SEQ ID NO 3
<211> LENGTH: 58
<212> TYPE: DNA
<213> ORGANISM: Artificial Sequence
<220> FEATURE:
<223> OTHER INFORMATION: Non-limiting Exemplary sequencing primer

<400> SEQUENCE: 3
aatgatacgg cgaccaccga gatctacact ctttccctac acgacgctct tccgatct       58

<210> SEQ ID NO 4
<211> LENGTH: 58
<212> TYPE: DNA
<213> ORGANISM: Artificial Sequence
<220> FEATURE:
<223> OTHER INFORMATION: Non-limiting Exemplary sequencing primer

<400> SEQUENCE: 4
caagcagaag acggcatacg agatgtgact ggagttcaga cgtgtgctct tccgatct       58
```

MOLECULAR INDEXING OF INTERNAL SEQUENCES

RELATED APPLICATIONS

The present application is a continuation of U.S. patent application Ser. No. 15/596,364, filed on May 16, 2017, which claims priority under 35 U.S.C. § 119(e) to U.S. Provisional Application No. 62/343,574, filed on May 31, 2016, which is herein expressly incorporated by reference in its entirety.

REFERENCE TO SEQUENCE LISTING

The present application is being filed along with a Sequence Listing in electronic format. The Sequence Listing is provided as a file entitled SEQUENCE_LISTING_68EB_298693_US2, created Mar. 31, 2020, which is 4 Kb in size, updated by a Replacement Electronic Sequence Listing file entitled AMENDED_SEQUENCE_LISTING_68EB_298693_US2, created Jun. 9, 2020, which is 4 Kb in size, and further updated by a Replacement Electronic Sequence Listing file entitled SECOND_AMENDED_SEQUENCE_LISTING_68EB_298693_US2, created Jul. 13, 2020, which is 4 Kb in size. The information in the electronic format of the Sequence Listings is incorporated herein by reference in its entirety.

BACKGROUND

Current methods of molecular barcoding and sequence analysis are typically limited to the 3'end of the target transcript, because molecular barcodes were attached to the 3' end, and Illumina sequencing length is short. Molecular barcoding of sequences upstream of transcript 3'end can be performed using gene-specific reverse transcription (RT) primers, the scalability is limited because RT primer with large amounts of molecular barcodes are designed against each gene, making it expensive to manufacture barcoded primers in a large gene pool. Methods for long read sequencing are limited by high sequencing error rates, low read throughput, and absence of molecular barcoding, which are aspects that prevent accurate sequence analysis, quantification, and lack of scalability.

SUMMARY

Some embodiments disclosed herein provide methods of labeling a target nucleic acid in a sample with a molecular barcode, comprising: hybridizing an oligonucleotide comprising a molecular barcode with a first nucleic acid molecule comprising the target nucleic acid; extending the oligonucleotide to generate a second nucleic acid molecule comprising the molecular barcode and the target nucleic acid; circularizing the second nucleic acid molecule or complement thereof to generate a circularized nucleic acid molecule comprising the molecular barcode in close proximity to the target nucleic acid; and amplifying the circularized nucleic acid molecule to generate a plurality of amplicons comprising the molecular barcode in close proximity to the target nucleic acid. In some embodiments, the methods further comprise synthesizing a complementary strand of the second nucleic acid molecule to generate a double-stranded nucleic acid molecule. In some embodiments, the circularizing comprises circularizing the double-stranded nucleic acid molecule. In some embodiments, the methods further comprise amplifying the second nucleic acid molecule or complement thereof to generate a copy of the second nucleic acid molecule or complement thereof. In some embodiments, the circularizing comprises circularizing a copy of the second nucleic acid molecule or complement thereof. In some embodiments, the methods further comprise sequencing the plurality of amplicons. In some embodiments, the first nucleic acid is an mRNA. In some embodiments, the oligonucleotide specifically binds to a binding site on the first nucleic acid molecule. In some embodiments, the binding site is a gene-specific sequence. In some embodiments, the binding site is a poly-A sequence. In some embodiments, the target nucleic acid comprises about 20 nt. In some embodiments, the target nucleic acid comprises about 30 nt. In some embodiments, the target nucleic acid comprises about 40 nt. In some embodiments, the binding site is at least 200 nt away from the target nucleic acid on the first nucleic acid molecule. In some embodiments, the binding site is at least 500 nt away from the target nucleic acid on the first nucleic acid molecule. In some embodiments, the binding site is at least 1,000 nt away from the target nucleic acid on the first nucleic acid molecule. In some embodiments, the binding site is at least 2,000 nt away from the target nucleic acid on the first nucleic acid molecule. In some embodiments, the molecular barcode comprises a sample label, a cellular label, a molecular label, or a combination thereof. In some embodiments, the molecular barcode comprises a binding site for a primer. In some embodiments, the primer is a universal primer. In some embodiments, the amplifying the circularized nucleic acid molecule comprises PCR amplification using a target-specific primer that specifically binds to the target nucleic acid or complement thereof. In some embodiments, the methods further comprise ligating an adaptor to the second nucleic acid molecule or complement thereof before the circularizing step. In some embodiments, the adaptor comprises a binding site for a second universal primer. In some embodiments, the amplifying the second nucleic acid molecule or complement thereof comprises PCR amplification using a second universal primer. In some embodiments, the target nucleic acid is a complementarity determining region (CDR) coding region of a T cell receptor gene. In some embodiments, the target nucleic acid is a complementarity determining region (CDR) coding region of an immunoglobulin gene. In some embodiments, the sample comprises a single cell. In some embodiments, the sample comprises a plurality of cells. In some embodiments, the oligonucleotide is immobilized on a solid support. In some embodiments, the solid support is a bead.

Some embodiments disclosed herein provide methods of labeling a target nucleic acid in a sample with a molecular barcode, comprising: hybridizing an oligonucleotide comprising a molecular barcode with a first nucleic acid molecule comprising the target nucleic acid; extending the oligonucleotide to generate a second nucleic acid molecule comprising the molecular barcode and the target nucleic acid; amplifying the second nucleic acid molecule or complement thereof to generate a first plurality of amplicons comprising the molecular barcode and the target nucleic acid; circularizing the first plurality of amplicons to generate a circularized nucleic acid molecule comprising the molecular barcode in close proximity to the target nucleic acid; and amplifying the circularized nucleic acid molecule to generate a second plurality of amplicons comprising the molecular barcode in close proximity to the target nucleic acid. In some embodiments, the methods further comprise sequencing the second plurality of amplicons. In some embodiments, the first nucleic acid is an mRNA. In some embodiments, the oligonucleotide specifically binds to a binding site on the first nucleic acid molecule. In some embodiments, the binding site is a gene-specific sequence. In some embodiments, the binding site is a poly-A sequence. In some embodiments, target nucleic acid comprises about 20 nt. In some embodiments, the target nucleic acid comprises about 30 nt. In some embodiments, the target nucleic acid comprises about 40 nt. In some embodiments, the binding site is at least 200 nt away from the target nucleic acid on the first nucleic acid molecule. In some embodiments, the binding site is at least 500 nt away from the target nucleic acid on the first nucleic acid molecule. In some embodiments, the binding site is at least 1,000 nt away from the target nucleic acid on the first nucleic acid molecule. In some embodiments, the binding site is at least 2,000 nt away from the target nucleic acid on the first nucleic acid molecule. In some embodiments, the molecular barcode comprises a sample label, a cellular label, a molecular label, or a combination thereof. In some embodiments, the molecular barcode comprises a binding site for a primer. In some embodiments, the primer is a universal primer. In some embodiments, the amplifying the circularized nucleic acid molecule comprises PCR amplification using a target-specific primer that specifically binds to the target nucleic acid or complement thereof. In some embodiments, the methods further comprise ligating an adaptor to the second nucleic acid molecule or complement thereof before the amplifying the second nucleic acid molecule or complement thereof step. In some embodiments, the adaptor comprises a binding site for a second universal primer. In some embodiments, the amplifying the second nucleic acid molecule or complement thereof comprises PCR amplification using a second universal primer. In some embodiments, the target nucleic acid is a complementarity determining region (CDR) coding region of a T cell receptor gene. In some embodiments, the target nucleic acid is a complementarity determining region (CDR) coding region of an immunoglobulin gene. In some embodiments, the sample comprises a single cell. In some embodiments, the sample comprises a plurality of cells. In some embodiments, the oligonucleotide is immobilized on a solid support. In some embodiments, the solid support is a bead.

Some embodiments disclosed herein provide methods of generating a sequencing library for a target nucleic acid molecule from a sample, comprising: hybridizing the target nucleic acid molecule with an oligonucleotide comprising a molecular barcode; extending the oligonucleotide to generate a second nucleic acid molecule comprising the molecular barcode and the target nucleic acid molecule; amplifying the second nucleic acid molecule or complement thereof to generate a first plurality of amplicons comprising the molecular barcode and the target nucleic acid molecule; fragmenting the first plurality of amplicons to generate a plurality of nucleic acid fragments comprising the molecular barcode and fragments of the target nucleic acid molecule, wherein at least two of the fragments of the target nucleic acid molecule have different length; circularizing the plurality of nucleic acid fragments to generate a plurality of circularized nucleic acid molecules, wherein at least two of the plurality of circularized nucleic acid molecules comprise the molecular barcode in close proximity to different positions of the target nucleic acid molecule; and amplifying the plurality of circularized nucleic acid molecules to generate a second plurality of amplicons, wherein at least two of the second plurality of amplicons comprises the molecular barcode in close proximity to different positions of the target nucleic acid molecule. In some embodiments, each of the plurality of nucleic acid fragments has a length from 50 nt to 10,000 nt. In some embodiments, the plurality of nucleic acid fragments comprises at least 2 nucleic acid fragments. In some embodiments, the plurality of nucleic acid fragments comprises at least 10 nucleic acid fragments. In some embodiments, the plurality of nucleic acid fragments comprises at least 100 nucleic acid fragments. In some embodiments, the plurality of nucleic acid fragments comprises at least 1,000 nucleic acid fragments. In some embodiments, the plurality of nucleic acid fragments comprises at least 10,000 nucleic acid fragments. In some embodiments, the fragmenting comprises sonication of the first plurality of amplicons. In some embodiments, the fragmenting comprises restriction digestion of the first plurality of amplicons. In some embodiments, at least 50% of the plurality of nucleic acid fragments comprises different length. In some embodiments, at least 80% of the plurality of nucleic acid fragments comprises different length. In some embodiments, at least 90% of the plurality of nucleic acid fragments comprises different length. In some embodiments, the target nucleic acid is a DNA. In some embodiments, the target nucleic acid is an mRNA. In some embodiments, the oligonucleotide specifically binds to a binding site on the target nucleic acid molecule. In some embodiments, the binding site is a gene-specific sequence. In some embodiments, the binding site is a poly-A sequence. In some embodiments, the molecular barcode comprises a sample label, a cellular label, a molecular label, or a combination thereof. In some embodiments, the molecular barcode comprises a binding site for a primer. In some embodiments, the primer is a universal primer. In some embodiments, the amplifying the plurality of circularized nucleic acid molecules comprises PCR amplification using the universal primer. In some embodiments, the methods further comprise ligating an adaptor to the second nucleic acid molecule or complement thereof before the amplifying step. In some embodiments, the adaptor comprises a binding site for a second universal primer. In some embodiments, the amplifying the second nucleic acid molecule or complement thereof comprises PCR amplification using a second universal primer. In some embodiments, the methods further comprise amplifying the second plurality of amplicons to generate a third plurality of amplicons. In some embodiments, the amplifying the second plurality of amplicons comprises PCR amplification using a random primer. In some embodiments, the random primer comprises a binding site for a sequencing primer. In some embodiments, at least two of the third plurality of amplicons overlap with each other. In some embodiments, the at least two of the third plurality of amplicons overlap with each other by at least 8 nt. In some embodiments, the at least two of the third plurality of amplicons overlap with each other by at least 10 nt. In some embodiments, the at least two of the third plurality of amplicons overlap with each other by at least 12 nt. In some embodiments, the at least two of the third plurality of amplicons overlap with each other by at least 14 nt. In some embodiments, the third plurality of amplicons covers the entire length of the nucleic acid molecule. In some embodiments, the third plurality of amplicons has an average size of about 250 nt. In some embodiments, the sample comprises a single cell. In some embodiments, the sample comprises a plurality of cells. In some embodiments, the oligonucleotide is immobilized on a solid support. In some embodiments, the solid support is a bead. In some embodiments, the methods further comprise generating a sequencing library for a plurality of target nucleic acid molecules from the sample.

Some embodiments disclosed herein provide compositions for generating a sequencing library for a plurality of nucleic acid molecules of a sample, comprising a plurality of oligonucleotides, wherein each of the plurality of oligonucleotides comprises from 5' to 3': a molecular label, a sample label, a binding site for a sequencing primer and a target-specific region that specifically binds to a nucleic acid molecule, wherein each of the plurality of oligonucleotides comprises the same sample label, and wherein at least 100 of the plurality of oligonucleotides comprise different molecular labels. In some embodiments, the binding site for the sequencing primer is oriented in the opposite direction of the oligonucleotide. In some embodiments, the target-specific region binds to each of the plurality of nucleic acid molecules. In some embodiments, the target-specific region comprises a random sequence. In some embodiments, the target-specific region comprises an oligo-dT sequence. In some embodiments, each of the plurality of oligonucleotides comprises a restriction enzyme recognition site 5' to the molecular label. In some embodiments, each of the plurality of oligonucleotides comprises a binding site for a universal primer 5' to the molecular label. In some embodiments, the binding site for a universal primer is 5' to the restriction enzyme recognition site. In some embodiments, the sample comprises a single cell. In some embodiments, the sample comprises a plurality of cells. In some embodiments, the oligonucleotide is immobilized on a solid support. In some embodiments, the solid support is a bead.

Some embodiments disclosed herein provide kits for generating a sequencing library for a plurality of nucleic acid molecules of a sample, comprising a plurality of oligonucleotides and an enzyme, wherein each of the plurality of oligonucleotides comprises from 5' to 3': a molecular label, a sample label, a binding site for a sequencing primer and a target-specific region that specifically binds to a nucleic acid molecule, wherein each of the plurality of oligonucleotides comprises the same sample label, and wherein at least 100 of the plurality of oligonucleotides comprise different molecular labels. In some embodiments, the binding site for a sequencing primer is oriented in the opposite direction of the oligonucleotide. In some embodiments, the target-specific region binds to each of the plurality of nucleic acid molecules. In some embodiments, the target-specific region comprises a random sequence. In some embodiments, the target-specific region comprises an oligo-dT sequence. In some embodiments, each of the plurality of oligonucleotides comprises a restriction enzyme recognition site 5' to the molecular label. In some embodiments, each of the plurality of oligonucleotides comprises a binding site for a universal primer 5' to the molecular label. In some embodiments, the binding site for a universal primer is 5' to the restriction enzyme recognition site. In some embodiments, the enzyme is selected from the group consisting of a ligase, a restriction enzyme, a DNA polymerase, a reverse transcriptase, an RNase, or any combination thereof. In some embodiments, the kits further comprise an adaptor. In some embodiments, the adaptor comprises a binding site for a second universal primer. In some embodiments, the kits further comprise a random primer. In some embodiments, the random primer comprises a binding site for a second sequencing primer. In some embodiments, the sample comprises a single cell. In some embodiments, the sample comprises a plurality of cells. In some embodiments, the oligonucleotide is immobilized on a solid support. In some embodiments, the solid support comprises a bead.

Some embodiments disclosed herein provide sequencing libraries for a nucleic acid molecule from a sample comprising a plurality of amplicons, wherein each of the plurality of amplicons comprises from 5' to 3': a binding site for a first sequencing primer, a molecular label, a fragment of the nucleic acid molecule and a binding site for a second sequencing primer, wherein each of the plurality of amplicons comprises the same molecular label, and wherein the fragments of the nucleic acid molecule of the plurality of amplicons cover the entire length of the nucleic acid molecule. In some embodiments, each of the plurality of amplicons comprises a sample label. In some embodiments, each of the plurality of amplicons comprises the same sample label. In some embodiments, the plurality of amplicons comprises an average size of 250 nt. In some embodiments, the plurality of amplicons comprises an average size of 500 nt. In some embodiments, the nucleic acid molecule is an mRNA. In some embodiments, the nucleic acid molecule has a length of at least 1,500 nt. In some embodiments, the nucleic acid molecule has a length of at least 3,000 nt. In some embodiments, the nucleic acid molecule has a length of at least 5,000 nt. In some embodiments, the sample comprises a single cell. In some embodiments, the sequencing libraries comprise at least 10 amplicons. In some embodiments, the sequencing libraries comprise at least 20 amplicons. In some embodiments, the sequencing libraries comprise at least 50 amplicons. In some embodiments, the sequencing libraries comprise at least 100 amplicons. In some embodiments, the sequencing libraries comprise at least 200 amplicons. In some embodiments, the sequencing libraries comprise at least 500 amplicons. In some embodiments, at least two of the fragments of the nucleic acid molecule overlap with each other. In some embodiments, the at least two of the fragments of the nucleic acid molecule overlap with each other by at least 8 nt. In some embodiments, the at least two of the fragments of the nucleic acid molecule overlap with each other by at least 10 nt. In some embodiments, the at least two of the fragments of the nucleic acid molecule overlap with each other by at least 12 nt. In some embodiments, the at least two of the fragments of the nucleic acid molecule overlap with each other by at least 14 nt.

DETAILED DESCRIPTION

Definitions

Figure 1:
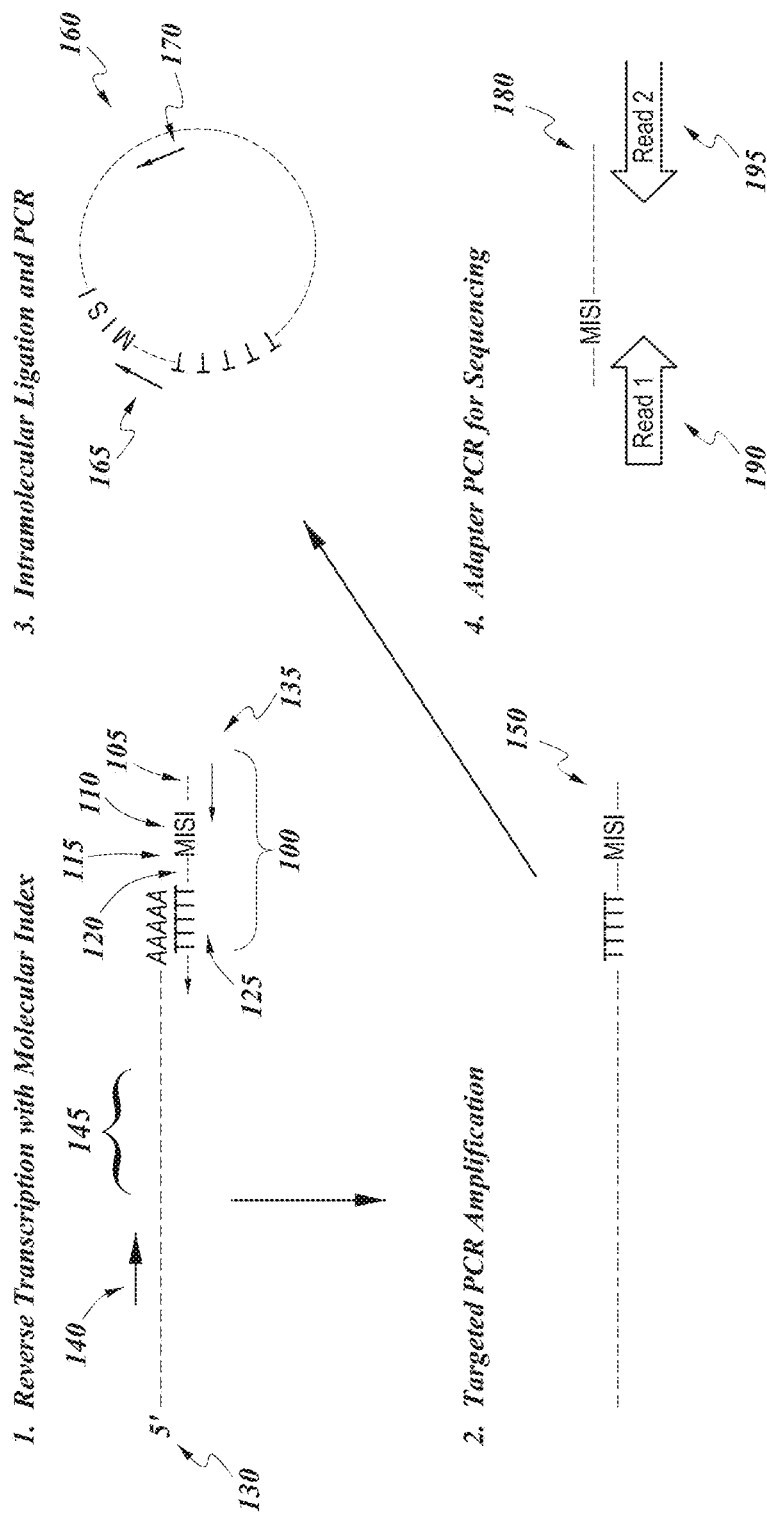
FIG. 1 shows a schematic illustration of an exemplary method of labeling a target nucleic acid with a molecular barcode.

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "attached", or "immobilized" to one another or to a common solid or semisolid surface. An association may refer to covalent or non-covalent means for attaching labels to solid or semi-solid supports such as beads. An association may comprise hybridization between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, a "nucleic acid" can generally refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone of the nucleic acid can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (Hpyrido(3',':4,5)pyrrolo [2,3-d] pyrimidin-2-one).

As used herein, the term "sample" can refer to a composition comprising targets. Suitable samples for analysis by the disclosed methods, devices, and systems include cells, single cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead." As used herein, "solid support" and "substrate" can be used interchangeably.

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids. As used herein, "target" can be used interchangeably with "species".

The term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the Lactococc s *lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

Methods of Labeling a Target Nucleic Acid

This disclosure provides methods that allow for labeling a target nucleic acid with one or more molecular barcodes, for example, through intramolecular ligation. The end products of these methods are suitable for, for example, sequence identification, transcript counting, alternative splicing analysis, mutation screening, and full length mRNA sequencing in a high throughput manner without the use of long read sequencing. The methods disclosed herein can be used for associating a molecular barcode with a target nucleic acid, wherein the target nucleic acid is located at the terminus or internally in a nucleic acid molecule, e.g., an mRNA molecule or a cDNA molecule. For example, the target nucleic acid can be located at least 200 nucleotides (nt), at least 300 nt, at least 400 nt, at least 500 nt, at least 600 nt, at least 700 nt, at least 800 nt, at least 900 nt, at least 1,000 nt, at least 2,000 nt, at least 3,000 nt, at least 4,000 nt, at least 5,000 nt, or more, from either the 5' end or the 3' end of the nucleic acid molecule.

Without being bound by any particular theory, the target nucleic acid can be a variety of sequences that are suitable for molecular barcoding, for example, a coding sequence for a functional domain, a mutation site, a splicing junction, a coding region, an untranslated region, etc. In some embodiments, the target nucleic acid can be any part of a nucleic acid molecule. In some embodiments, the nucleic acid molecule can comprise a T cell receptor gene, an immunoglobulin gene, an MHC gene, a tumor suppressor gene, an oncogene, a transcription factor gene, a cell-surface gene, etc. In some embodiments, the target nucleic acid can comprise about 20 nt, about 30 nt, about 40 nt, about 50 nt, about 60 nt, about 70 nt, about 80 nt, about 90 nt, about 100 nt, about 200 nt, about 300 nt, about 400 nt, about 500 nt, or a range between any two of the above values.

Hybridizing an Oligonucleotide with a Nucleic Acid Molecule

In some embodiments, a nucleic acid molecule comprising a target nucleic acid is hybridized to an oligonucleotide comprising a molecular barcode. The oligonucleotide can be a variety of lengths, such as about 20 nt, about 30 nt, about 40 nt, about 50 nt, about 60 nt, about 70 nt, about 80 nt, about 90 nt, about 100 nt, about 200 nt, or more, or a range between any two of the above values. The molecular barcode can comprise, or be, a molecular label, a sample label, a cellular label, a universal label, or any combination thereof.

In some embodiments, the oligonucleotide can comprise a binding region that specifically binds to a binding site on the nucleic acid molecule. The binding site can be, or comprise, for example, a gene-specific sequence, a poly-A sequence, a 5' sequence, a 3' sequence, or a combination thereof. It would be appreciated that the binding site can be located at various distances from the target nucleic acid on the nucleic acid molecule. For example, on the nucleic acid molecule, the binding site can be located at least 20 nt, at least 50 nt, at least 100 nt, at least 200 nt, at least 300 nt, at least 400 nt, at least 500 nt, at least 600 nt, at least 700 nt, at least 800 nt, at least 900 nt, at least 1,000 nt, at least 2,000 nt, at least 3,000 nt, at least 4,000 nt, at least 5,000 nt, or more, from the target nucleic acid. In some embodiments, the binding site is located 20 nt, 50 nt, 100 nt, 200 nt, 300 nt, 400 nt, 500 nt, 600 nt, 700 nt, 800 nt, 900 nt, 1,000 nt, 2,000 nt, 3,000 nt, 4,000 nt, 5,000 nt, or a range between any two of these values, from the target nucleic acid on the nucleic acid molecule.

Extension

In some embodiments, the hybridized oligonucleotides can be extended using the nucleic acid molecule as a template to generate a new oligonucleotide comprising a molecular barcode. In some embodiments where the nucleic acid molecule is an RNA molecule, the oligonucleotide can be extended using reverse transcription. Reverse transcription of the associated RNA molecule may occur by the addition of a reverse transcriptase And cDNA molecules can be generated by the reverse transcription reactions. In some embodiments, a second strand DNA is generated using the cDNA molecules as a template. Second strand synthesis can be performed using a primer that is specific for the nucleic acid molecule. It would be appreciated that the primer preferably binds to the cDNA molecule at a location that is away from the target nucleic acid. In some embodiments, the primer can bind to the cDNA molecule at a location that is about 10 nt, about 20 nt, about 30 nt, about 40 nt, about 50 nt, about 100 nt, a range between any two of these values, or more away from the target nucleic acid.

Amplification of Extension Products

In some embodiments, the extension product, the cDNA from the reverse transcription step or the double-stranded DNA can be used as a template for amplification. One or more nucleic acid amplification reactions can be performed to create multiple copies of the molecular labeled nucleic acid molecules. In some embodiments, the amplification can be performed using a universal primer that binds to a binding site on the oligonucleotide.

Amplification can be performed using a primer that is specific for the nucleic acid molecule. It would be appreciated that the primer preferably binds to the extension product, the cDNA from the reverse transcription step or the double-stranded DNA at a location that is away from the target nucleic acid. In some embodiments, the primer can bind to the extension product (for example, the cDNA from the reverse transcription step or the double-stranded DNA) at a location that is about 10 nt, about 20 nt, about 30 nt, about 40 nt, about 50 nt, about 100 nt, a range between any two of these values, or more away from the target nucleic acid. In some embodiments, the extension product (for example, the cDNA from the reverse transcription step or the double-stranded DNA) can be ligated with an adaptor. In some embodiments, the adaptor can comprise a binding site for a second universal primer. The second universal primer can be used, for example, for the amplification of the extension product (e.g., the cDNA from the reverse transcription step or the double-stranded DNA).

The term "adaptor" can refer to a single stranded, partially double-stranded, or double-stranded, oligonucleotide of at least 5, 10, 15, 20 or 25 bases that can be attached to the end of a nucleic acid. Adaptor sequences can comprise, for example, priming sites, the complement of a priming site, and recognition sites for endonucleases, common sequences and promoters. The adaptor can be entirely or substantially double stranded. A double stranded adaptor can comprise two oligonucleotides that are at least partially complementary. The adaptor can be phosphorylated or unphosphorylated on one or both strands. The adaptor can have a double-stranded section and a single-stranded overhang section that is completely or partially complementary to an overhang (e.g., generated by a restriction enzyme, or a polymerase enzyme). The overhang in the adaptor can be, for example, 4 to 8 bases. For example, when DNA is digested with the restriction enzyme EcoRI, the resulting double stranded fragments are flanked at either end by the single stranded overhang 5'-AATT-3', an adaptor that carries a single stranded overhang 5'-AATT-3' can hybridize to the fragment through complementarity between the overhanging regions. This "sticky end" hybridization of the adaptor to the fragment facilitates ligation of the adaptor to the fragment; however, blunt ended ligation is also possible. Blunt ends can be converted to sticky ends using, for example, the exonuclease activity of the Klenow fragment. For example when DNA is digested with PvuII, the blunt ends can be converted to a two base pair overhang by incubating the fragments with Klenow in the presence of dTTP and dCTP. Overhangs can also be converted to blunt ends by filling in an overhang or removing an overhang.

Amplification may be performed in a multiplexed manner, wherein multiple nucleic acid sequences are amplified simultaneously. The amplification reactions may comprise amplifying at least a portion of a sample label, if present. The amplification reactions may comprise amplifying at least a portion of the cellular and/or molecular label. The amplification reactions may comprise amplifying at least a portion of a sample tag, a cellular label, a spatial label, a molecular label, a target nucleic acid, or a combination thereof. The amplification reactions may comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids. The amplification reactions may comprise amplifying 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range of any two of these values, of the plurality of nucleic acids.

In some embodiments, amplification is performed using a polymerase chain reaction (PCR). As used herein, PCR refers to a reaction for the in vitro amplification of specific DNA sequences by the simultaneous primer extension of complementary strands of DNA. As used herein, PCR encompasses derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), whole transcriptome amplification (WTA), whole genome amplification (WGA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some instances, the amplification may not produce circularized transcripts.

Amplification may comprise use of one or more non-natural nucleotides. Non-natural nucleotides may comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides may be added to one or more cycles of an amplification reaction. The addition of the non-natural nucleotides may be used to identify products as specific cycles or time points in the amplification reaction.

Conducting the one or more amplification reactions may comprise the use of one or more primers. The one or more primers may comprise at least 1, 2, 3, 4, 5, 6, 7, 8, 9, 10, 11, 12, 13, 14, or 15 or more nucleotides. The one or more primers may comprise at least 1, 2, 3, 4, 5, 6, 7, 8, 9, 10, 11, 12, 13, 14, or 15 or more nucleotides. The one or more primers may comprise less than 12-15 nucleotides. The one or more primers may anneal to at least a portion of the molecular barcoded nucleic acid molecules. The one or more primers may anneal to the 3' end or 5' end of the molecular barcoded nucleic acid molecules. The one or more primers may anneal to an internal region of the molecular barcoded nucleic acid molecules. The internal region may be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends of the molecular labeled reference gene(s) and/or spike-in RNA. The one or more primers may comprise a fixed panel of primers. The one or more primers may comprise at least one or more customized primers. The one or more primers may comprise at least one or more control primers. The one or more primers may comprise at least one or more gene-specific primers.

The one or more primers may comprise any universal primer of the disclosure. The universal primer may anneal to a universal primer binding site. The one or more customized primers may anneal to a sample label, a spatial label, a cellular label, a molecular label, a target, or any combination thereof. The one or more primers can, in some embodiments, comprise one or more of a universal primer and a customized primer. The customized primer may be designed to specifically amplify the molecular barcoded nucleic acid molecules. The one or more primers may comprise at least 96 or more customized primers. The one or more primers may comprise at least 960 or more customized primers. The one or more primers may comprise at least 9600 or more customized primers. The one or more customized primers may anneal to two or more different barcoded nucleic acid molecules. The two or more different barcoded nucleic acid molecules may correspond to one or more genes.

Circularization of Extension/Amplification Products

In the methods described herein, he extension product (e.g., the cDNA from the reverse transcription step, the double-stranded DNA, etc.) or the amplification product thereof can be circularized through, e.g., intramolecular ligation. In some embodiments, the intramolecular ligation can be performed on a single-stranded DNA. In some embodiments, the intramolecular ligation can be performed on a double-stranded DNA. In some embodiments, the intramolecular ligation is performed on the cDNA obtained from the reverse transcription step, or complement thereof. In some embodiments, the intramolecular ligation is performed on amplicons of the cDNA or complement thereof. In some embodiments, the intramolecular ligation is performed on one of the strands of the amplicons of the cDNA.

As a result of the intramolecular ligation, a circularized nucleic acid molecule (single-stranded or double-stranded) is produced. Without being bound by any particular theory, in the circularized nucleic acid molecule, the molecular barcode, or part thereof, can be in close proximity to the target nucleic acid. For example, in the circularized nucleic acid molecule, the molecular barcode, or part thereof, can be at most 500 nt, at most 400 nt, at most 300 nt, at most 200 nt, at most 100 nt, at most 90 nt, at most 80 nt, at most 70 nt, at most 60 nt, at most 50 nt, at most 40 nt, at most 30 nt, at most 20 nt, at most 10 nt, or less, away from the target nucleic acid. In some embodiments, in the circularized nucleic acid molecule, the molecular barcode, or part thereof, is, or is about, 1000 nt, 750 nt, 500 nt, 400 nt, 300 nt, 200 nt, 100 nt, 90 nt, 80 nt, 70 nt, 60 nt, 50 nt, 40 nt, 30 nt, 20 nt, 10 nt, or a range between any two of these values, away from the target nucleic acid.

Amplifying the Circularization Product

As described herein, the circularization product can be amplified to produce a plurality of amplicons comprising the molecular barcode in close proximity to the target nucleic acid. In some embodiments, the plurality amplicons comprises, or are, linear amplicons.

Amplification can be performed, for example, using a primer that is specific for the nucleic acid molecule. It would be appreciated that the primer preferably binds to the circularization product at a location that is away from the target nucleic acid. In some embodiments, the primer can bind to the circularization product at a location that is about 10 nt, about 20 nt, about 30 nt, about 40 nt, about 50 nt, about 100 nt, or a range between any two of these values, away from the target nucleic acid. In some embodiments, the primer can bind to the circularization product at a location that is at least, or at least about, 10 nt, 20 nt, 30 nt, 40 nt, 50 nt, 100 nt, or more, away from the target nucleic acid. In some embodiments, the primer can bind to the circularization product at a location that is at most, or at most about, 10 nt, 20 nt, 30 nt, 40 nt, 50 nt, 100 nt, or more, away from the target nucleic acid.

Amplification may be performed in a multiplexed manner, wherein multiple nucleic acid sequences are amplified simultaneously. The amplification reactions may comprise amplifying at least a portion of a sample label, if present. The amplification reactions may comprise amplifying at least a portion of the cellular and/or molecular label. The amplification reactions may comprise amplifying at least a portion of a sample tag, a cellular label, a spatial label, a molecular label, a target nucleic acid, or a combination thereof. The amplification reactions may comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the circularization products. The amplification reactions may comprise amplifying 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range between any two of these values, of the circularization products.

In some embodiments, the amplification is performed using a polymerase chain reaction (PCR). As used herein, PCR may refer to a reaction for the in vitro amplification of specific DNA sequences by the simultaneous primer extension of complementary strands of DNA. As used herein, PCR may encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), whole transcriptome amplification (WTA), whole genome amplification (WGA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some instances, the amplification may not produce circularized transcripts.

Amplification may comprise use of one or more non-natural nucleotides. Non-natural nucleotides may comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides may be added to one or more cycles of an amplification reaction. The addition of the non-natural nucleotides may be used to identify products as specific cycles or time points in the amplification reaction.

Conducting the one or more amplification reactions may comprise the use of one or more primers. The one or more primers may comprise at least 1, 2, 3, 4, 5, 6, 7, 8, 9, 10, 11, 12, 13, 14, or 15 or more nucleotides. The one or more primers may comprise at least 1, 2, 3, 4, 5, 6, 7, 8, 9, 10, 11, 12, 13, 14, or 15 or more nucleotides. The one or more primers may comprise less than 12-15 nucleotides. The one or more primers may anneal to at least a portion of the molecular barcoded nucleic acid molecules. The one or more primers may anneal to an internal region of the circularization product. The one or more primers may comprise at least one or more customized primers. The one or more primers may comprise at least one or more control primers. The one or more primers may comprise at least one or more gene-specific primers.

The one or more primers may comprise any universal primer of the disclosure. The universal primer may anneal to a universal primer binding site. The one or more customized primers may anneal to a first sample label, a second sample label, a spatial label, a cellular label, a molecular label, a target, or any combination thereof. The one or more primers may comprise a universal primer and a customized primer. The customized primer may be designed to amplify the circularization product. The one or more primers may comprise at least 96 or more customized primers. The one or more primers may comprise at least 960 or more customized primers. The one or more primers may comprise at least 9600 or more customized primers. The one or more customized primers may anneal to two or more different circularization product. The two or more different circularization product may correspond to one or more genes.

Any amplification scheme can be used in the methods of the present disclosure. For example, in one embodiments, the first round PCR can amplify molecules (e.g., attached to the bead) using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and molecular index on read 1, the gene on read 2, and the sample index on index 1 read.

Amplification can be performed in one or more rounds. In some instances there are multiple rounds of amplification. Amplification can comprise two or more rounds of amplification. The first amplification can be an extension to generate the gene specific region. The second amplification can occur when a sample nucleic hybridizes to the newly generated strand.

Sequencing

The amplicons comprising the molecular barcode in close proximity to the target nucleic acid (for example, the linear amplicons) can be subject to sequencing reactions to determine the target nucleic acid sequence, the molecular barcode or part thereof, or both. Any suitable sequencing method known in the art can be used, preferably high-throughput approaches. For example, cyclic array sequencing using platforms such as Roche 454, Illumina Solexa, ABI-SOLiD, ION Torrent, Complete Genomics, Pacific Bioscience, Helicos, or the Polonator platform, may also be utilized. Sequencing may comprise MiSeq sequencing. Sequencing may comprise HiSeq sequencing.

In some embodiments, sequencing can comprise sequencing at least about 10, 20, 30, 40, 50, 60, 70, 80, 90, 100 or more nucleotides or base pairs of the labeled nucleic acid and/or molecular barcode. In some embodiments, sequencing can comprise sequencing at most about 10, 20, 30, 40, 50, 60, 70, 80, 90, 100 or more nucleotides or base pairs of the labeled nucleic acid and/or molecular barcode. In some embodiments, sequencing can comprise sequencing at least about 200, 300, 400, 500, 600, 700, 800, 900, 1,000 or more nucleotides or base pairs of the labeled nucleic acid and/or molecular barcode. In some embodiments, sequencing can comprise sequencing at most about 200, 300, 400, 500, 600, 700, 800, 900, 1,000 or more nucleotides or base pairs of the labeled nucleic acid and/or stochastic barcode. In some embodiments, sequencing can comprise sequencing at least about 1,500; 2,000; 3,000; 4,000; 5,000; 6,000; 7,000; 8,000; 9,000; or 10,000 or more nucleotides or base pairs of the labeled nucleic acid and/or stochastic barcode. In some embodiments, sequencing can comprise sequencing at most about 1,500; 2,000; 3,000; 4,000; 5,000; 6,000; 7,000; 8,000; 9,000; or 10,000 or more nucleotides or base pairs of the labeled nucleic acid and/or molecular barcode.

In some embodiments, sequencing can comprise at least about 200, 300, 400, 500, 600, 700, 800, 900, 1,000 or more sequencing reads per run. In some embodiments, sequencing can comprise at most about 200, 300, 400, 500, 600, 700, 800, 900, 1,000 or more sequencing reads per run. In some embodiments, sequencing comprises sequencing at least about 1,500; 2,000; 3,000; 4,000; 5,000; 6,000; 7,000; 8,000; 9,000; or 10,000 or more sequencing reads per run. In some embodiments, sequencing comprises sequencing at most about 1,500; 2,000; 3,000; 4,000; 5,000; 6,000; 7,000; 8,000; 9,000; or 10,000 or more sequencing reads per run. In some embodiments, sequencing can comprise sequencing at least 10, 50, 100, 150, 200, 250, 300, 350, 400, 450, 500, 550, 600, 650, 700, 750, 800, 850, 900, 950 or 1000 or more millions of sequencing reads per run. In some embodiments, sequencing can comprise sequencing at most 10, 50, 100, 150, 200, 250, 300, 350, 400, 450, 500, 550, 600, 650, 700, 750, 800, 850, 900, 950 or 1000 or more millions of sequencing reads per run. In some embodiments, sequencing can comprise sequencing at least 100, 200, 300, 400, 500, 600, 700, 800, 900, 1000, 1100, 1200, 1300, 1400, 1500, 1600, 2000, 3000, 4000, or 5000 or more millions of sequencing reads in total. In some embodiments, sequencing can comprise sequencing at most 100, 200, 300, 400, 500, 600, 700, 800, 900, 1000, 1100, 1200, 1300, 1400, 1500, 1600, 2000, 3000, 4000, or 5000 or more millions of sequencing reads in total. In some embodiments, sequencing can comprise less than or equal to about 1,600,000,000 sequencing reads per run. In some embodiments, sequencing can comprise less than or equal to about 200,000,000 reads per run.

An exemplary method for labeling a target nucleic acid is illustrated in FIG. 1. As shown, an mRNA molecule 130 can be hybridized to an oligonucleotide 100, which can comprise a binding site for a universal primer 105, a sample label 110, a molecular label 115, a binding site for a second universal primer 120, and an oligo-dT 125. After a reverse transcription step to generate a cDNA 150, a primer 140 that specifically binds to the cDNA at a location beyond the target nucleic acid 145 and a universal primer that binds to the binding site 105 are used to amplify the cDNA 150. The amplification product is denatured to single-stranded DNA molecules which are circularized by intramolecular ligation to produce a circularized DNA molecule 160. Another PCR amplification reaction is conducted using a second universal primer 165 and a primer 170 that binds to the circularized DNA molecule 160 at a location beyond the target nucleic acid 145, to produce a linearized amplicon 180. The linearized amplicon 180 can be amplified using primers 190 and 195 which comprise binding sites for sequencing primers. In some embodiments, the target nucleic acid 145 can be a CDR3 sequence in a T cell receptor gene.

Methods of Generating Sequencing Library

Some embodiments disclosed herein provide methods of generating a sequencing library for a target nucleic acid molecule from a sample. In some embodiments, the target nucleic acid molecule is a DNA, a cDNA, a genomic DNA, an mRNA, or a combination thereof. In some embodiments, the target nucleic acid molecule can comprise unknown sequences. In some embodiments, the target nucleic acid molecule can be at least 1,000 nt, at least 2,000 nt, at least 3,000 nt, at least 4,000 nt, at least 5,000 nt, at least 6,000 nt, at least 7,000 nt, at least 8,000 nt, at least 9,000 nt, at least 10,000 nt, at least 20,000 nt, at least 50,000 nt, at least 100,000 nt, or more, in length.

Hybridizing an Oligonucleotide with a Target Nucleic Acid Molecule

In some embodiments, a target nucleic acid molecule comprising a target nucleic acid is hybridized to an oligonucleotide comprising a molecular barcode. The oligonucleotide can be a variety of lengths, such as about 20 nt, about 30 nt, about 40 nt, about 50 nt, about 60 nt, about 70 nt, about 80 nt, about 90 nt, about 100 nt, about 200 nt, or more, or a range between any two of the above values. The molecular barcode can comprise a molecular label, a sample label, a cellular label, a universal label, or any combination thereof. In some embodiments, the oligonucleotide can comprise a restriction site.

In some embodiments, the oligonucleotide can comprise a binding region that specifically binds to a binding site on the target nucleic acid molecule. The binding site can be, or comprise, a gene-specific sequence, a poly-A sequence, a 5' sequence, a 3' sequence, or a combination thereof.

Extension

In some embodiments, the hybridized oligonucleotides can be extended using the target nucleic acid molecule as a template. In some embodiments where the nucleic acid molecule is an RNA molecule, the oligonucleotide can be extended using reverse transcription. Reverse transcription of the associated RNA molecule may occur by the addition of a reverse transcriptase. cDNA molecules are generated by the reverse transcription reactions. In some embodiments, a second strand DNA is generated using the cDNA molecules as a template. Second strand synthesis can be performed using a primer that is specific for the target nucleic acid molecule.

Amplification of Extension Products

In some embodiments, the extension product, the cDNA from the reverse transcription step or the double-stranded DNA can be used as a template for amplification. One or more nucleic acid amplification reactions may be performed to create multiple copies of the molecular labeled target nucleic acid molecules. In some embodiments, the amplification can be performed using a universal primer that binds to a binding site on the oligonucleotide.

Amplification can be performed using a primer that is specific for the target nucleic acid molecule. In some embodiments, the extension product, the cDNA from the reverse transcription step or the double-stranded DNA can be ligated with an adaptor. In some embodiments, the adaptor can comprise a binding site for a second universal primer. The second universal primer can be used for the amplification of the extension product, the cDNA from the reverse transcription step or the double-stranded DNA.

Adaptor sequences can be synthesized using for example, priming sites, the complement of a priming site, and recognition sites for endonucleases, common sequences and promoters. The adaptor can be entirely or substantially double stranded. A double stranded adaptor can comprise two oligonucleotides that are at least partially complementary. The adaptor can be phosphorylated or unphosphorylated on one or both strands. The adaptor can have a double stranded section and a single stranded overhang section that is completely or partially complementary to an overhang (e.g., generated by a restriction enzyme, or a polymerase enzyme). The overhang in the adaptor can be, for example, 4 to 8 bases. For example, when DNA is digested with the restriction enzyme EcoRI, the resulting double stranded fragments are flanked at either end by the single stranded overhang 5'-AATT-3', an adaptor that carries a single stranded overhang 5'-AATT-3' can hybridize to the fragment through complementarity between the overhanging regions. This "sticky end" hybridization of the adaptor to the fragment facilitates ligation of the adaptor to the fragment; however, blunt ended ligation is also possible. Blunt ends can be converted to sticky ends using, for example, the exonuclease activity of the Klenow fragment. For example when DNA is digested with PvuII the blunt ends can be converted to a two base pair overhang by incubating the fragments with Klenow in the presence of dTTP and dCTP. Overhangs can also be converted to blunt ends by filling in an overhang or removing an overhang.

Amplification may be performed in a multiplexed manner, wherein multiple nucleic acid sequences are amplified simultaneously. The amplification reactions may comprise amplifying at least a portion of a sample label, if present. The amplification reactions may comprise amplifying at least a portion of the cellular and/or molecular label. The amplification reactions may comprise amplifying at least a portion of a sample tag, a cellular label, a spatial label, a molecular label, a target nucleic acid, or a combination thereof. The amplification reactions may comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

In some embodiments, amplification may be performed using a polymerase chain reaction (PCR). As used herein, PCR may refer to a reaction for the in vitro amplification of specific DNA sequences by the simultaneous primer extension of complementary strands of DNA. As used herein, PCR may encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), whole transcriptome amplification (WTA), whole genome amplification (WGA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some instances, the amplification may not produce circularized transcripts.

Amplification may comprise use of one or more non-natural nucleotides. Non-natural nucleotides may comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides may be added to one or more cycles of an amplification reaction. The addition of the non-natural nucleotides may be used to identify products as specific cycles or time points in the amplification reaction.

Conducting the one or more amplification reactions may comprise the use of one or more primers. The one or more primers may comprise at least 1, 2, 3, 4, 5, 6, 7, 8, 9, 10, 11, 12, 13, 14, or 15 or more nucleotides. The one or more primers may comprise at least 1, 2, 3, 4, 5, 6, 7, 8, 9, 10, 11, 12, 13, 14, or 15 or more nucleotides. The one or more primers may comprise less than 12-15 nucleotides. The one or more primers may anneal to at least a portion of the molecular barcoded nucleic acid molecules. The one or more primers may anneal to the 3' end or 5' end of the molecular barcoded nucleic acid molecules. The one or more primers may anneal to an internal region of the molecular barcoded nucleic acid molecules. The internal region may be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends of the molecular labeled reference gene(s) and/or spike-in RNA. The one or more primers may comprise a fixed panel of primers. The one or more primers may comprise at least one or more customized primers. The one or more primers may comprise at least one or more control primers. The one or more primers may comprise at least one or more gene-specific primers.

The one or more primers may comprise any universal primer of the disclosure. The universal primer may anneal to a universal primer binding site. The one or more customized primers may anneal to a first sample label, a second sample label, a spatial label, a cellular label, a molecular label, a target, or any combination thereof. The one or more primers may comprise a universal primer and a customized primer. The customized primer may be designed to amplify the molecular barcoded nucleic acid molecules. The one or more primers may comprise at least 96 or more customized primers. The one or more primers may comprise at least 960 or more customized primers. The one or more primers may comprise at least 9600 or more customized primers. The one or more customized primers may anneal to two or more different barcoded nucleic acid molecules. The two or more different barcoded nucleic acid molecules may correspond to one or more genes.

Fragmentation of Amplification Products

The amplification products can be fragmented to produce a plurality of nucleic acid fragments. In some embodiments, the fragmentation can be partial fragmentation, so that fragments of the target nucleic acid molecule can have different lengths. Fragmentation can be conducted by, for example, sonication, restriction enzyme digestion, or any other suitable methods. In some embodiments, two or more of the plurality of nucleic acid fragments have the same 5' terminus but different 3' terminus. In some embodiments, two or more of the plurality of nucleic acid fragments have the same 3' terminus but different 5' terminus. In some embodiments, each of the plurality of nucleic acid fragments has a length between 50 nt to 10,000 nt. In some embodiments, the plurality of nucleic acid fragments comprises at least 2 nucleic acid fragments. In some embodiments, the plurality of nucleic acid fragments comprises at least 10 nucleic acid fragments. In some embodiments, the plurality of nucleic acid fragments comprises at least 100 nucleic acid fragments. In some embodiments, the plurality of nucleic acid fragments comprises at least 1,000 nucleic acid fragments. In some embodiments, the plurality of nucleic acid fragments comprises at least 10,000 nucleic acid fragments. In some embodiments, the fragmenting comprises restriction digestion of the first plurality of amplicons. In some embodiments, at least 50% of the plurality of nucleic acid fragments comprises different length. In some embodiments, at least 80% of the plurality of nucleic acid fragments comprises different length. In some embodiments, at least 90% of the plurality of nucleic acid fragments comprises different length.

In some embodiments, the fragments can be subject to purification (e.g., washing) to remove fragments that do not comprise the molecular barcode. For example, the fragments can be immobilized to a solid support through the oligonucleotide, and unbound fragments can be removed.

Circularization of Fragments

In some embodiments, the fragments of the target nucleic acid molecule can be circularized through, e.g., intramolecular ligation. In some embodiments, the intramolecular ligation can be performed on a single-stranded DNA. In some embodiments, the intramolecular ligation can be performed on a double-stranded DNA.

As a result of the intramolecular ligation, circularized nucleic acid molecules having various sizes are produced.

Amplifying the Circularization Product

As described herein, the circularization product can be amplified to produce a plurality of amplicons comprising the molecular barcode associated with fragments of the target nucleic acid molecule. In some embodiments, the plurality amplicons comprises, or is, linear amplicons.

Amplification can be performed, for example, using a universal primer that binds to a binding site on the oligonucleotide. In some embodiments, two universal primers that bind to the oligonucleotide in opposite directions can be used to linearize the circulated product.

Amplification may be performed in a multiplexed manner, wherein multiple nucleic acid sequences are amplified simultaneously. The amplification reactions may comprise amplifying at least a portion of a sample label, if present. The amplification reactions may comprise amplifying at least a portion of the cellular and/or molecular label. The amplification reactions may comprise amplifying at least a portion of a sample tag, a cellular label, a spatial label, a molecular label, a target nucleic acid, or a combination thereof. The amplification reactions may comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the circularization products. The amplification reactions may comprise amplifying 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range between any two of these values, of the circularization products.

In some embodiments, the amplification is performed using a polymerase chain reaction (PCR). As used herein, PCR may refer to a reaction for the in vitro amplification of specific DNA sequences by the simultaneous primer extension of complementary strands of DNA. As used herein, PCR may encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), whole transcriptome amplification (WTA), whole genome amplification (WGA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some instances, the amplification may not produce circularized transcripts.

Amplification may comprise use of one or more non-natural nucleotides. Non-natural nucleotides may comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides may be added to one or more cycles of an amplification reaction. The addition of the non-natural nucleotides may be used to identify products as specific cycles or time points in the amplification reaction.

Conducting the one or more amplification reactions may comprise the use of one or more primers. The one or more primers may comprise at least 1, 2, 3, 4, 5, 6, 7, 8, 9, 10, 11, 12, 13, 14, or 15 or more nucleotides. The one or more primers may comprise at least 1, 2, 3, 4, 5, 6, 7, 8, 9, 10, 11, 12, 13, 14, or 15 or more nucleotides. The one or more primers may comprise less than 12-15 nucleotides. The one or more primers may anneal to at least a portion of the molecular barcoded nucleic acid molecules. The one or more primers may anneal to an internal region of the circularization product. The one or more primers may comprise at least one or more customized primers. The one or more primers may comprise at least one or more control primers. The one or more primers may comprise at least one or more gene-specific primers.

The one or more primers may comprise any universal primer of the disclosure. The universal primer may anneal to a universal primer binding site. The one or more customized primers may anneal to a first sample label, a second sample label, a spatial label, a cellular label, a molecular label, a target, or any combination thereof. The one or more primers may comprise a universal primer and a customized primer. The customized primer may be designed to amplify the circularization product. The one or more primers may comprise at least 96 or more customized primers. The one or more primers may comprise at least 960 or more customized primers. The one or more primers may comprise at least 9600 or more customized primers. The one or more customized primers may anneal to two or more different circularization product. The two or more different circularization product may correspond to one or more genes.

Any amplification scheme can be used in the methods of the present disclosure. For example, in one scheme, the first round PCR can amplify molecules (e.g., attached to the bead) using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and molecular index on read 1, the gene on read 2, and the sample index on index 1 read.

Amplification can be performed in one or more rounds. In some instances there are multiple rounds of amplification. Amplification can comprise two or more rounds of amplification. The first amplification can be an extension to generate the gene specific region. The second amplification can occur when a sample nucleic hybridizes to the newly generated strand.

Sequencing

The amplicons comprising the molecular barcode associated with fragments of the target nucleic acid molecule (for example, the linear amplicons) can be subject to sequencing reactions to determine the target nucleic acid sequence, the molecular barcode or part thereof, or both. Any suitable sequencing method known in the art can be used, preferably high-throughput approaches. For example, cyclic array sequencing using platforms such as Roche 454, Illumina Solexa, ABI-SOLiD, ION Torrent, Complete Genomics, Pacific Bioscience, Helicos, or the Polonator platform, may also be utilized. Sequencing may comprise MiSeq sequencing. Sequencing may comprise HiSeq sequencing.

In some embodiments, sequencing can comprise sequencing at least about 10, 20, 30, 40, 50, 60, 70, 80, 90, 100 or more nucleotides or base pairs of the labeled nucleic acid and/or molecular barcode. In some embodiments, sequencing can comprise sequencing at most about 10, 20, 30, 40, 50, 60, 70, 80, 90, 100 or more nucleotides or base pairs of the labeled nucleic acid and/or molecular barcode. In some embodiments, sequencing can comprise sequencing at least about 200, 300, 400, 500, 600, 700, 800, 900, 1,000 or more nucleotides or base pairs of the labeled nucleic acid and/or molecular barcode. In some embodiments, sequencing can comprise sequencing at most about 200, 300, 400, 500, 600, 700, 800, 900, 1,000 or more nucleotides or base pairs of the labeled nucleic acid and/or stochastic barcode. In some embodiments, sequencing can comprise sequencing at least about 1,500; 2,000; 3,000; 4,000; 5,000; 6,000; 7,000; 8,000; 9,000; or 10,000 or more nucleotides or base pairs of the labeled nucleic acid and/or stochastic barcode. In some embodiments, sequencing can comprise sequencing at most about 1,500; 2,000; 3,000; 4,000; 5,000; 6,000; 7,000; 8,000; 9,000; or 10,000 or more nucleotides or base pairs of the labeled nucleic acid and/or molecular barcode.

In some embodiments, sequencing can comprise at least about 200, 300, 400, 500, 600, 700, 800, 900, 1,000 or more sequencing reads per run. In some embodiments, sequencing can comprise at most about 200, 300, 400, 500, 600, 700, 800, 900, 1,000 or more sequencing reads per run. In some embodiments, sequencing comprises sequencing at least about 1,500; 2,000; 3,000; 4,000; 5,000; 6,000; 7,000; 8,000; 9,000; or 10,000 or more sequencing reads per run. In some embodiments, sequencing comprises sequencing at most about 1,500; 2,000; 3,000; 4,000; 5,000; 6,000; 7,000; 8,000; 9,000; or 10,000 or more sequencing reads per run. In some embodiments, sequencing can comprise sequencing at least 10, 50, 100, 150, 200, 250, 300, 350, 400, 450, 500, 550, 600, 650, 700, 750, 800, 850, 900, 950 or 1000 or more millions of sequencing reads per run. In some embodiments, sequencing can comprise sequencing at most 10, 50, 100, 150, 200, 250, 300, 350, 400, 450, 500, 550, 600, 650, 700, 750, 800, 850, 900, 950 or 1000 or more millions of sequencing reads per run. In some embodiments, sequencing can comprise sequencing at least 100, 200, 300, 400, 500, 600, 700, 800, 900, 1000, 1100, 1200, 1300, 1400, 1500, 1600, 2000, 3000, 4000, or 5000 or more millions of sequencing reads in total. In some embodiments, sequencing can comprise sequencing at most 100, 200, 300, 400, 500, 600, 700, 800, 900, 1000, 1100, 1200, 1300, 1400, 1500, 1600, 2000, 3000, 4000, or 5000 or more millions of sequencing reads in total. In some embodiments, sequencing can comprise less than or equal to about 1,600,000,000 sequencing reads per run. In some embodiments, sequencing can comprise less than or equal to about 200,000,000 reads per run.

Figure 2:
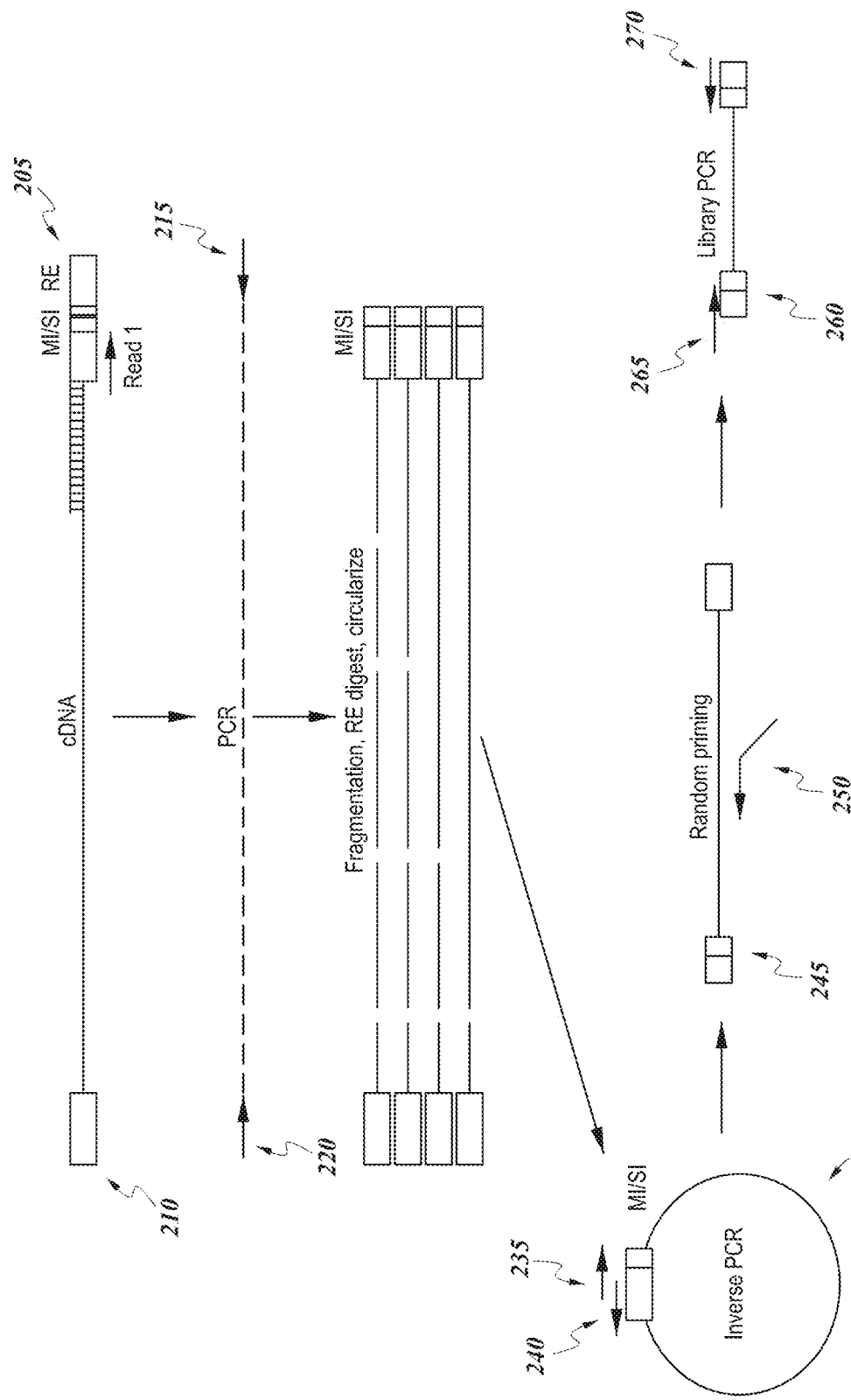
FIG. 2 shows a schematic illustration of an exemplary method of generating a sequencing library for a target nucleic acid molecule.

FIG. 2 shows a schematic illustration of an exemplary method to produce a sequencing library of a target nucleic acid molecule. In a first step, a cDNA is produced by reverse transcription of an mRNA molecule using an oligonucleotide 205 comprising a restriction site, a binding site for a universal primer 215, a sample label, a molecular label, a binding site for a second universal primer 235, a binding site for a third universal primer 240, and a poly dT. A adaptor 210 having a binding site for primer 220 is ligated to the cDNA. Universal primers 215 and 220 are used to amplify the cDNA to produce a plurality of amplicons. The plurality of amplicons is partially digested to produce fragments of varying sizes, which are ligated to produce a plurality of circularized products 230 having different sizes. Inverse PCR using universal primers 235 and 240 is used to produce a plurality of linearized amplicons 245. PCR reaction using universal primer 235 and random primer 250 is used to generate a second plurality of amplicons 260. Universal primers 265 and 270 are used to amplify the second plurality of amplicons 260 to generate a sequencing library.

Compositions for Generating Sequencing Library

Some embodiments disclosed herein provide composition for generating a sequencing library for a plurality of nucleic acid molecules of a sample. In some embodiments, the compositions can comprise a plurality of oligonucleotides, wherein each of the plurality of oligonucleotides comprises from 5' to 3': a molecular label, a sample label, a binding site for a sequencing primer and a target-specific region that specifically binds to a nucleic acid molecule. In some embodiments, the binding site for the sequencing primer is oriented in the opposite direction of the oligonucleotide. In some embodiments, each of the plurality of oligonucleotides comprises a restriction enzyme recognition site 5' to the molecular label. In some embodiments, each of the plurality of oligonucleotides comprises a binding site for a universal primer 5' to the molecular label. In some embodiments, the oligonucleotide can further comprise a binding site for a second universal primer 3' to the binding site for the sequencing primer, and oriented in the opposite direction of the binding site for the sequencing primer. An exemplary oligonucleotide has the following sequence: 3' VTTTTTTTTTTTTTTTTTTTGCTGCGAGAAGGCTA-GANNNNNNNNNNNNNNNNCGC TAGCGGTTACAG-GAGGTCTGGAGGACATTGGCGAT 5' (SEQ ID NO:1), wherein the "V" represents A, G or C, the "NNNNNNNN" at nucleotides 37-44 represents the sequence for the sample label, the "NNNNNNNN" at nucleotides 45-52 represents the sequence for the molecular label, the "CGCTAGCG" is an AsiSI restriction site. Another exemplary oligonucleotide has the following sequence: 3' TTTTTTTTTTTTTTTTTTTGCTGCGAGAAGGCTA-GANNNNNNNNNNNNNNNNCGC TAGCGGTTACAG-GAGGTCTGGAGGACATTGGCGAT 5' (SEQ ID NO:2), wherein the "NNNNNNNN" at nucleotides 37-44 represents the sequence for the sample label, the "NNNNNNNN" at nucleotides 45-52 represents the sequence for the molecular label, the "CGCTAGCG" is an AsiSI restriction site.

Kits

Some embodiments disclosed herein provide kits for generating a sequencing library for a plurality of nucleic acid molecules of a sample, comprising a plurality of oligonucleotides as disclosed herein, and an enzyme. In some embodiments, each of the plurality of oligonucleotides comprises from 5' to 3': a molecular label, a sample label, a binding site for a sequencing primer and a target-specific region that specifically binds to a nucleic acid molecule. In some embodiments, the binding site for the sequencing primer is oriented in the opposite direction of the oligonucleotide. In some embodiments, each of the plurality of oligonucleotides comprises a restriction enzyme recognition site 5' to the molecular label. In some embodiments, each of the plurality of oligonucleotides comprises a binding site for a universal primer 5' to the molecular label. In some embodiments, the oligonucleotide can further comprise a binding site for a second universal primer 3' to the binding site for the sequencing primer, and oriented in the opposite direction of the binding site for the sequencing primer. In some embodiments, enzyme is selected from the group consisting of a ligase, a restriction enzyme, a DNA polymerase, a reverse transcriptase, an RNase, or any combination thereof.

The kit can, in some embodiments, comprise one or more substrates (e.g., microwell array, Pixel device), either as a free-standing substrate (or chip) comprising one or more microwell arrays, or packaged within one or more flow-cells or cartridges. The kits can comprise one or more solid support suspensions, wherein the individual solid supports within a suspension comprise a plurality of attached stochastic barcodes of the disclosure. The kits can comprise stochastic barcodes that may not be attached to a solid support. In some embodiments, the kit may further comprise a mechanical fixture for mounting a free-standing substrate in order to create reaction wells that facilitate the pipetting of samples and reagents into the substrate. The kit may further comprise reagents, e.g. lysis buffers, rinse buffers, or hybridization buffers, for performing the stochastic barcoding assay. The kit may further comprise reagents (e.g. enzymes, primers, dNTPs, NTPs, RNAse inhibitors, or buffers) for performing nucleic acid extension reactions, for example, reverse transcription reactions and primer extension reactions. The kit may further comprise reagents (e.g. enzymes, universal primers, sequencing primers, target-specific primers, or buffers) for performing amplification reactions to prepare sequencing libraries.

The kit can, in some embodiments, comprise sequencing library amplification primers of the disclosure. The kit may comprise a second strand synthesis primer of the disclosure. The kit can comprise any primers of the disclosure (e.g., gene-specific primers, random multimers, sequencing primers, and universal primers).

The kit can, in some embodiments, comprise one or more molds, for example, molds comprising an array of micropillars, for casting substrates (e.g., microwell arrays), and one or more solid supports (e.g., bead), wherein the individual beads within a suspension comprise a plurality of attached stochastic barcodes of the disclosure. The kit may further comprise a material for use in casting substrates (e.g. agarose, a hydrogel, PDMS, optical adhesive. and the like).

The kit can, in some embodiments, comprise one or more substrates that are pre-loaded with solid supports comprising a plurality of attached stochastic barcodes of the disclosure. In some instances, there can be one solid support per microwell of the substrate. In some embodiments, the plurality of stochastic barcodes may be attached directly to a surface of the substrate, rather than to a solid support. In any of these embodiments, the one or more microwell arrays can be provided in the form of free-standing substrates (or chips), or they may be packed in flow-cells or cartridges.

In some embodiments, the kit can comprise one or more cartridges that incorporate one or more substrates. In some embodiments, the one or more cartridges further comprises one or more pre-loaded solid supports, wherein the individual solid supports within a suspension comprise a plurality of attached stochastic barcodes of the disclosure. In some embodiments, the beads can be pre-distributed into the one or more microwell arrays of the cartridge. In some embodiments, the beads, in the form of suspensions, can be pre-loaded and stored within reagent wells of the cartridge. In some embodiments, the one or more cartridges may further comprise other assay reagents that are pre-loaded and stored within reagent reservoirs of the cartridges.

Kits can generally include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by the disclosure. Such media can include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

The kit can comprise the device as described in U.S. application Ser. No. 14/508,911 is herein incorporated by reference in its entirety.

The kit can comprise one or more of the rFit User Guide, SDS for kit reagents, rFit RT Primer Mix, 10 mM Tris HCl, pH 8.0, rFit 2×RT Reaction Mix, rFit RT Enzyme Mix, Spike-in RNA control 1 ng/µL, rFit 2×PCR Master Mix, rFit PCR Primer Mix, Spike-In PCR Primer Mix, Hybridization Buffer Mix, A 16-well detector cartridge with adhesive cover, or any combination thereof.

The kit may require the user to provide certain reagents. For example, the user may need to provide reagents such as: RNase-free water (Ambion, cat no. AM9932), Wash A (Affymetrix, cat no. 900721), Wash B (Affymetrix, cat no. 900722), and Lens Paper (Tiffen, cat no. 154 6027T), or any combination thereof.

The user may need to provide consumables such as RNase-free filter pipette tips (Rainin), 0.2 mL PCR tubes, and 1.5 mL microcentrifuge tubes, or any combination thereof.

The user may need to provide equipment such as: Pipettes (1 µL-1000 µL volume capability), Microcentrifuge for 1.5-2.0 mL tubes, Microcentrifuge for 0.2 mL reaction tubes, Vortexer, Thermal cycler with heated lid, Microplate Incubator/Hybridization Oven (MiuLab, cat no. MT70-2, joyfay.com), and CR Imager (Cellular Research), or any combination thereof.

Sequencing Libraries

Some embodiments disclosed herein provide sequencing libraries for a nucleic acid molecule from a sample comprising a plurality of amplicons, wherein each of the plurality of amplicons comprises from 5' to 3': a binding site for a first sequencing primer, a molecular label, a fragment of the nucleic acid molecule and a binding site for a second sequencing primer. In some embodiments, each of the plurality of amplicons comprises the same molecular label. In some embodiments, the fragments of the nucleic acid molecule of the plurality of amplicons cover the entire length of the nucleic acid molecule.

In some embodiments, each of the plurality of amplicons comprises a sample label. In some embodiments, each of the plurality of amplicons comprises the same sample label. In some embodiments, the plurality of amplicons comprises an average size of 250 nt. In some embodiments, the plurality of amplicons comprises an average size of 500 nt. In some embodiments, the nucleic acid molecule has a length of at least 1,500 nt. In some embodiments, the nucleic acid molecule has a length of at least 3,000 nt. In some embodiments, the nucleic acid molecule has a length of at least 5,000 nt. In some embodiments, the sample comprises a single cell. In some embodiments, the sequencing libraries comprise at least 10 amplicons. In some embodiments, the sequencing libraries comprise at least 20 amplicons. In some embodiments, the sequencing libraries comprise at least 50 amplicons. In some embodiments, the sequencing libraries comprise at least 100 amplicons. In some embodiments, the sequencing libraries comprise at least 200 amplicons. In some embodiments, the sequencing libraries comprise at least 500 amplicons. In some embodiments, at least two of the fragments of the nucleic acid molecule overlap with each other. In some embodiments, the at least two of the fragments of the nucleic acid molecule overlap with each other by at least 8 nt. In some embodiments, the at least two of the fragments of the nucleic acid molecule overlap with each other by at least 10 nt. In some embodiments, the at least two of the fragments of the nucleic acid molecule overlap with each other by at least 12 nt. In some embodiments, the at least two of the fragments of the nucleic acid molecule overlap with each other by at least 14 nt.

Figure 3:
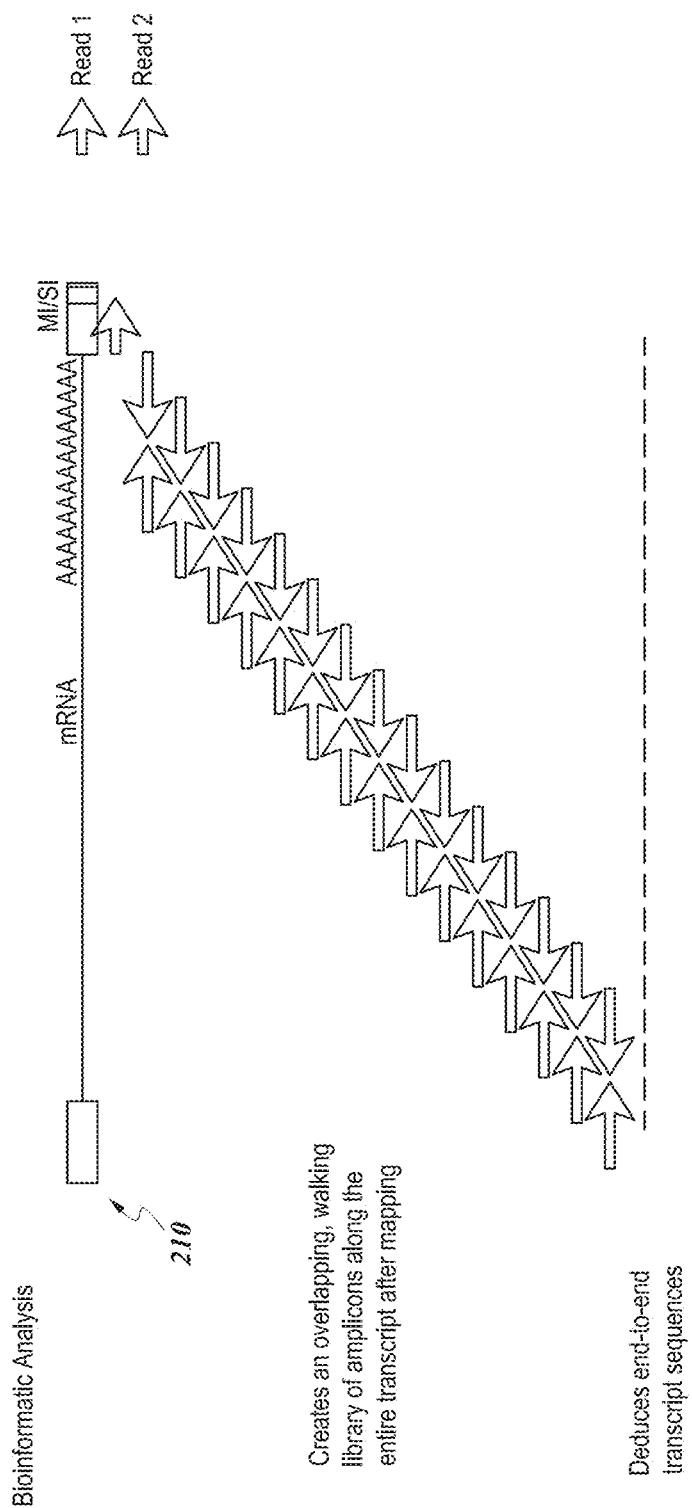
FIG. 3 shows a schematic illustration of an exemplary method of generating a sequencing library for a target nucleic acid molecule.

FIG. 3 shows a schematic illustration of an exemplary sequencing library. An oligonucleotide is used to generate a cDNA 305. An adaptor 310 is ligated to the cDNA 305. Following amplification, fragmentation, circularization and amplification steps as shown in FIG. 2, a sequencing library comprising overlapping fragments of the cDNA 305 and flanked by sequencing primer binding sites 315 and 320 is generated. Non-limiting Exemplary sequencing primers are: 5'-AATGATACGGCGACCACCGAGATCTA-CACTCTTTCCCTACACGACGCTCTTCCGA TCT-3' (SEQ ID NO:3) and 5'-CAAGCAGAAGACGGCAT-ACGAGATIGTGACTGGAGTTCA-GACGTGTGCTCTTCCG ATCT-3' (SEQ ID NO:4).

Methods of Analyzing Sequencing Reads

Some embodiments disclosed herein provide methods for analyzing the sequencing reads of the sequencing libraries disclosed herein. In some embodiments, sequencing reads that contain proper sample labels are sorted into corresponding 'bins' to sort sequencings reads from the same sample origin. Within each sample, sequencing reads with the same molecular label are mapped either to the whole transcriptome or a set of expected target sequences. Sequencing reads that map to the same gene or target with the same molecular label are likely from the same original target nucleic acid molecule, such as an mRNA, hence a computational analysis can be performed to 1) count the number of molecular labels found per gene for gene expression profiling; and/or 2) assemble small fragment reads that map to the same gene/transcript and molecular label to determine the full length sequence, partial sequence, and/or splice variants.

Samples
Cells

A sample for use in the method, compositions, systems, and kits of the disclosure can comprise one or more cells. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some instances, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma.

In some embodiments, the cells are cells that have been infected with virus and contain viral oligonucleotides. In some embodiments, the viral infection can be caused by a virus selected from the group consisting of double-stranded DNA viruses (e.g. adenoviruses, herpes viruses, pox viruses), single-stranded (+ strand or "sense") DNA viruses (e.g. parvoviruses), double-stranded RNA viruses (e.g. reoviruses), single-stranded (+ strand or sense) RNA viruses (e.g. picornaviruses, togaviruses), single-stranded (− strand or antisense) RNA viruses (e.g. orthomyxoviruses, rhabdoviruses), single-stranded ((+ strand or sense) RNA viruses with a DNA intermediate in their life-cycle) RNA-RT viruses (e.g. retroviruses), and double-stranded DNA-RT viruses (e.g. hepadnaviruses). Exemplary viruses can include, but are not limited to, SARS, HIV, coronaviruses, Ebola, Malaria, Dengue, Hepatitis C, Hepatitis B, and Influenza.

In some embodiments, the cells are bacterial cells. These can include cells from gram-positive bacterial and/or gram-negative bacteria. Examples of bacteria that may be analyzed using the disclosed methods, devices, and systems include, but are not limited to, Actinomedurae, *Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like. Gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like. Other bacteria may include *Myobacterium avium, Myobacterium leprae, Myobacterium tuberculosis, Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci* and the like.

In some embodiments, the cells are cells from fungi. Non-limiting examples of fungi that may be analyzed using the disclosed methods, devices, and systems include, but are not limited to, *Aspergilli, Candidae, Candida albicans, Coccidioides immitis, Cryptococci*, and combinations thereof.

In some embodiments, the cells are cells from protozoans or other parasites. Examples of parasites to be analyzed using the methods, devices, and systems of the present disclosure include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae, trapezoidal amoeba*, worms (e.g., helminthes), particularly parasitic worms including, but not limited to, Nematoda (roundworms, e.g., whipworms, hookworms, pinworms, ascarids, filarids and the like), Cestoda (e.g., tapeworms).

As used herein, the term "cell" can refer to one or more cells. In some embodiments, the cells are normal cells, for example, human cells in different stages of development, or human cells from different organs or tissue types (e.g. white blood cells, red blood cells, platelets, epithelial cells, endothelial cells, neurons, glial cells, fibroblasts, skeletal muscle cells, smooth muscle cells, gametes, or cells from the heart, lungs, brain, liver, kidney, spleen, pancreas, thymus, bladder, stomach, colon, small intestine). In some embodiments, the cells can be undifferentiated human stem cells, or human stem cells that have been induced to differentiate. In some embodiments, the cells can be fetal human cells. The fetal human cells can be obtained from a mother pregnant with the fetus. In some embodiments, the cells are rare cells. A rare cell can be, for example, a circulating tumor cell (CTC), circulating epithelial cell, circulating endothelial cell, circulating endometrial cell, circulating stem cell, stem cell, undifferentiated stem cell, cancer stem cell, bone marrow cell, progenitor cell, foam cell, mesenchymal cell, trophoblast, immune system cell (host or graft), cellular fragment, cellular organelle (e.g. mitochondria or nuclei), pathogen infected cell, and the like.

In some embodiments, the cells are non-human cells, for example, other types of mammalian cells (e.g. mouse, rat, pig, dog, cow, or horse). In some embodiments, the cells are other types of animal or plant cells. In some embodiments, the cells can be any prokaryotic or eukaryotic cells.

In some embodiments, a first cell sample is obtained from a person not having a disease or condition, and a second cell sample is obtained from a person having the disease or condition. In some embodiments, the persons are different. In some embodiments, the persons are the same but cell samples are taken at different time points. In some embodiments, the persons are patients, and the cell samples are patient samples. The disease or condition can be a cancer, a bacterial infection, a viral infection, an inflammatory disease, a neurodegenerative disease, a fungal disease, a parasitic disease, a genetic disorder, or any combination thereof.

In some embodiments, cells suitable for use in the presently disclosed methods can range in size, for example ranging from about 2 micrometers to about 100 micrometers in diameter. In some embodiments, the cells can have diameters of at least 2 micrometers, at least 5 micrometers, at least 10 micrometers, at least 15 micrometers, at least 20 micrometers, at least 30 micrometers, at least 40 micrometers, at least 50 micrometers, at least 60 micrometers, at least 70 micrometers, at least 80 micrometers, at least 90 micrometers, or at least 100 micrometers. In some embodiments, the cells can have diameters of at most 100 micrometers, at most 90 micrometers, at most 80 micrometers, at most 70 micrometers, at most 60 micrometers, at most 50 micrometers, at most 40 micrometers, at most 30 micrometers, at most 20 micrometers, at most 15 micrometers, at most 10 micrometers, at most 5 micrometers, or at most 2 micrometers. The cells can have a diameter of any value within a range, for example from about 5 micrometers to about 85 micrometers. In some embodiments, the cells have diameters of about 10 micrometers.

In some embodiments, the cells are sorted prior to associating one or more of the cells with a bead and/or in a microwell. For example the cells can be sorted by fluorescence-activated cell sorting or magnetic-activated cell sorting, or e.g., by flow cytometry. The cells can be filtered by size. In some instances a retentate contains the cells to be associated with the bead. In some instances the flow through contains the cells to be associated with the bead.

Molecular Barcodes

A molecular barcode can refer to a polynucleotide sequence that may be used to stochastically label (e.g., barcode, tag) a target. A molecular barcode can comprise one or more labels. Exemplary labels include, but are not limited to, a universal label, a cellular label, a molecular label, a sample label, a plate label, a spatial label, and/or a pre-spatial label. A molecular barcode can comprise a 5' amine that may link the molecular barcode to a solid support. The molecular barcode can comprise one or more of a universal label, a cellular label, and a molecular label. The universal label may be 5'-most label. The molecular label may be the 3'-most label. In some instances, the universal label, the cellular label, and the molecular label are in any order. The molecular barcode can comprise a target-binding region. The target-binding region can interact with a target (e.g., target nucleic acid, RNA, mRNA, DNA) in a sample. For example, a target-binding region can comprise an oligo dT sequence which can interact with poly-A tails of mRNAs. In some instances, the labels of the molecular barcode (e.g., universal label, dimension label, spatial label, cellular label, and molecular label) may be separated by 1, 2, 3, 4, 5, 6, 7, 8, 9, 10, 11, 12, 13, 14, 15, 16, 17, 18, 19, or 20 or more nucleotides.

A molecular barcode can, in some embodiments, comprise one or more universal labels. The one or more universal labels may be the same for all stochastic barcodes in the set of stochastic barcodes (e.g., attached to a given solid support). In some embodiments, the one or more universal labels may be the same for all molecular barcodes attached to a plurality of beads. In some embodiments, a universal label may comprise a nucleic acid sequence that is capable of hybridizing to a sequencing primer. Sequencing primers may be used for sequencing molecular barcodes comprising a universal label. Sequencing primers (e.g., universal sequencing primers) may comprise sequencing primers associated with high-throughput sequencing platforms. In some embodiments, a universal label may comprise a nucleic acid sequence that is capable of hybridizing to a PCR primer. In some embodiments, the universal label may comprise a nucleic acid sequence that is capable of hybridizing to a sequencing primer and a PCR primer. The nucleic acid sequence of the universal label that is capable of hybridizing to a sequencing or PCR primer may be referred to as a primer binding site. A universal label may comprise a sequence that may be used to initiate transcription of the stochastic barcode. A universal label may comprise a sequence that may be used for extension of the stochastic barcode or a region within the stochastic barcode. A universal label may be at least about 1, 2, 3, 4, 5, 10, 15, 20, 25, 30, 35, 40, 45, 50 or more nucleotides in length. A universal label may comprise at least about 10 nucleotides. A universal label may be at most about 1, 2, 3, 4, 5, 10, 15, 20, 25, 30, 35, 40, 45, 50 or more nucleotides in length. In some embodiments, a cleavable linker or modified nucleotide may be part of the universal label sequence to enable the molecular barcode to be cleaved off from the support. As used herein, a universal label can be used interchangeably with "universal PCR primer."

A molecular barcode can comprise a dimension label. A dimension label can comprise a nucleic acid sequence that provides information about a dimension in which the stochastic labeling occurred. For example, a dimension label can provide information about the time at which a target was stochastically barcoded. A dimension label can be associated with a time of stochastic barcoding in a sample. A dimension label can activated at the time of molecular labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with stochastic barcodes at the G1 phase of the cell cycle. The cells can be pulsed again with stochastic barcodes at the S phase of the cell cycle, and so on. Stochastic barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific timepoint. The activatable dimension label may be constitutively activated (e.g., not turned off). The activatable dimension label can be reversibly activated (e.g., the activatable dimension label can be turned on and turned off). The dimension label can be reversibly activatable at least 1, 2, 3, 4, 5, 6, 7, 8, 9, or 10 or more times. The dimension label can be reversibly activatable at least 1, 2, 3, 4, 5, 6, 7, 8, 9, or 10 or more times. The dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging, photocleavage), and introduction of a non-natural nucleotide.

The dimension label can be identical for all molecular barcodes attached to a given solid support (e.g., bead), but different for different solid supports (e.g., beads). In some embodiments, at least 60%, 70%, 80%, 85%, 90%, 95%, 97%, 99% or 100% of molecular barcodes on the same solid support may comprise the same dimension label. In some embodiments, at least 60% of molecular barcodes on the same solid support may comprise the same dimension label. In some embodiments, at least 95% of molecular barcodes on the same solid support may comprise the same dimension label.

There may be as many as $10^6$ or more unique dimension label sequences represented in a plurality of solid supports (e.g., beads). A dimension label may be at least about 1, 2, 3, 4, 5, 10, 15, 20, 25, 30, 35, 40, 45, 50 or more nucleotides in length. A dimension label may be at most about 300, 200, 100, 90, 80, 70, 60, 50, 40, 30, 20, 15, 12, 10, 9, 8, 7, 6, 5, 4 or fewer or more nucleotides in length. A dimension label may comprise from about 5 to about 200 nucleotides. A dimension label may comprise from about 10 to about 150 nucleotides. A dimension label may comprise from about 20 to about 125 nucleotides in length.

A molecular barcode can comprise a spatial label. A spatial label can comprise a nucleic acid sequence that provides information about the spatial orientation of a target molecule which is associated with the stochastic barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some instances, multiple spatial labels are used together to encode one or more positions in space.

The spatial label can be identical for all stochastic barcodes attached to a given solid support (e.g., bead), but different for different solid supports (e.g., beads). In some embodiments, at least 60%, 70%, 80%, 85%, 90%, 95%, 97%, 99% or 100% of molecular barcodes on the same solid support may comprise the same spatial label. In some embodiments, at least 60% of stochastic barcodes on the same solid support may comprise the same spatial label. In some embodiments, at least 95% of molecular barcodes on the same solid support may comprise the same spatial label.

There may be as many as $10^6$ or more unique spatial label sequences represented in a plurality of solid supports (e.g., beads). A spatial label may be at least about 1, 2, 3, 4, 5, 10, 15, 20, 25, 30, 35, 40, 45, 50 or more nucleotides in length. A spatial label may be at most about 300, 200, 100, 90, 80, 70, 60, 50, 40, 30, 20, 15, 12, 10, 9, 8, 7, 6, 5, 4 or fewer or more nucleotides in length. A spatial label may comprise from about 5 to about 200 nucleotides. A spatial label may comprise from about 10 to about 150 nucleotides. A spatial label may comprise from about 20 to about 125 nucleotides in length.

Molecular barcodes may comprise a cellular label. A cellular label may comprise a nucleic acid sequence that provides information for determining which target nucleic acid originated from which cell. In some embodiments, the cellular label is identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support may comprise the same cellular label. In some embodiments, at least 60% of stochastic barcodes on the same solid support may comprise the same cellular label. In some embodiment, at least 95% of molecular barcodes on the same solid support may comprise the same cellular label.

There may be as many as $10^6$ or more unique cellular label sequences represented in a plurality of solid supports (e.g., beads). A cellular label may be at least about 1, 2, 3, 4, 5, 10, 15, 20, 25, 30, 35, 40, 45, 50 or more nucleotides in length. A cellular label may be at most about 300, 200, 100, 90, 80, 70, 60, 50, 40, 30, 20, 15, 12, 10, 9, 8, 7, 6, 5, 4 or fewer or more nucleotides in length. A cellular label may comprise from about 5 to about 200 nucleotides. A cellular label may comprise from about 10 to about 150 nucleotides. A cellular label may comprise from about 20 to about 125 nucleotides in length.

Molecular barcodes may comprise a molecular label. A molecular label may comprise a nucleic acid sequence that provides identifying information for the specific type of target nucleic acid species hybridized to the stochastic barcode. A molecular label may comprise a nucleic acid sequence that provides a counter for the specific occurrence of the target nucleic acid species hybridized to the stochastic barcode (e.g., target-binding region). In some embodiments, a diverse set of molecular labels are attached to a given solid support (e.g., bead). In some embodiments, there may be as many as $10^6$ or more unique molecular label sequences attached to a given solid support (e.g., bead). In some embodiments, there may be as many as $10^5$ or more unique molecular label sequences attached to a given solid support (e.g., bead). In some embodiments, there may be as many as $10^4$ or more unique molecular label sequences attached to a given solid support (e.g., bead). In some embodiments, there may be as many as $10^3$ or more unique molecular label sequences attached to a given solid support (e.g., bead). In some embodiments, there may be as many as $10^2$ or more unique molecular label sequences attached to a given solid support (e.g., bead). A molecular label may be at least about 1, 2, 3, 4, 5, 10, 15, 20, 25, 30, 35, 40, 45, 50 or more nucleotides in length. A molecular label may be at most about 300, 200, 100, 90, 80, 70, 60, 50, 40, 30, 20, 15, 12, 10, 9, 8, 7, 6, 5, 4 or fewer nucleotides in length.

Molecular barcodes may comprise a target binding region. In some embodiments, the target binding regions may comprise a nucleic acid sequence that hybridizes specifically to a target (e.g., target nucleic acid, target molecule, e.g., a cellular nucleic acid to be analyzed), for example to a specific gene sequence. In some embodiments, a target binding region may comprise a nucleic acid sequence that may attach (e.g., hybridize) to a specific location of a specific target nucleic acid. In some embodiments, the target binding region may comprise a nucleic acid sequence that is capable of specific hybridization to a restriction site overhang (e.g. an EcoRI sticky-end overhang). The molecular barcode may then ligate to any nucleic acid molecule comprising a sequence complementary to the restriction site overhang.

A molecular barcode can comprise a target-binding region. A target-binding region can hybridize with a target of interest. For example, a target-binding region can comprise an oligo dT which can hybridize with mRNAs comprising poly-adenylated ends. A target-binding region can be gene-specific. For example, a target-binding region can be configured to hybridize to a specific region of a target. A target-binding region can be at least 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 or more nucleotides in length. A target-binding region can be at most 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 or more nucleotides in length. A target-binding region can be from 5-30 nucleotides in length. When a stochastic barcode comprises a gene-specific target-binding region, the stochastic barcode can be referred to as a gene-specific stochastic barcode.

A target binding region may comprise a non-specific target nucleic acid sequence. A non-specific target nucleic acid sequence may refer to a sequence that may bind to multiple target nucleic acids, independent of the specific sequence of the target nucleic acid. For example, target binding region may comprise a random multimer sequence, or an oligo-dT sequence that hybridizes to the poly-A tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all stochastic barcodes attached to a given bead. In some embodiments, the target binding regions for the plurality of stochastic barcodes attached to a given bead may comprise two or more different target binding sequences. A target binding region may be at least about 5, 10, 15, 20, 25, 30, 35, 40, 45, 50 or more nucleotides in length. A target binding region may be at most about 5, 10, 15, 20, 25, 30, 35, 40, 45, 50 or more nucleotides in length.

A molecular barcode can comprise an orientation property which can be used to orient (e.g., align) the stochastic barcodes. A molecular barcode can comprise a moiety for isoelectric focusing. Different molecular barcodes can comprise different isoelectric focusing points. When these molecular barcodes are introduced to a sample, the sample can undergo isoelectric focusing in order to orient the stochastic barcodes into a known way. In this way, the orientation property can be used to develop a known map of stochastic barcodes in a sample. Exemplary orientation properties can include, electrophoretic mobility (e.g., based on size of the stochastic barcode), isoelectric point, spin, conductivity, and/or self-assembly. For example, molecular barcodes can comprise an orientation property of self-assembly, can self-assemble into a specific orientation (e.g., nucleic acid nanostructure) upon activation.

A molecular barcode can comprise an affinity property. A spatial label can comprise an affinity property. An affinity property can be include a chemical and/or biological moiety that can facilitate binding of the stochastic barcode to another entity (e.g., cell receptor).

The cellular label and/or any label of the disclosure may further comprise a unique set of nucleic acid sub-sequences of defined length, e.g. 7 nucleotides each (equivalent to the number of bits used in some Hamming error correction codes), which are designed to provide error correction capability. The set of error correction sub-sequences comprise 7 nucleotide sequences can be designed such that any pairwise combination of sequences in the set exhibits a defined "genetic distance" (or number of mismatched bases), for example, a set of error correction sub-sequences may be designed to exhibit a genetic distance of 3 nucleotides. In some embodiments, the length of the nucleic acid sub-sequences used for creating error correction codes may vary, for example, they may be at least 3 nucleotides, at least 7 nucleotides, at least 15 nucleotides, or at least 31 nucleotides in length. In some embodiments, nucleic acid sub-sequences of other lengths may be used for creating error correction codes.

Molecular barcodes of the disclosure can comprise error-correcting sequences (e.g., Hamming codes) in them for error-correction. A Hamming code can refer an arithmetic process that identifies unique binary codes based upon inherent redundancy that are capable of correcting single bit errors. For example, a Hamming code can be matched with a nucleic acid barcode in order to screen for single nucleotide errors occurring during nucleic acid amplification. The identification of a single nucleotide error by using a Hamming code, thereby can allow for the correction of the nucleic acid barcode.

When a molecular barcode comprises more than one of a type of label (e.g., more than one cellular label or more than one molecular label), the labels may be interspersed with a linker label sequence. A linker label sequence may be at least about 5, 10, 15, 20, 25, 30, 35, 40, 45, 50 or more nucleotides in length. A linker label sequence may be at most about 5, 10, 15, 20, 25, 30, 35, 40, 45, 50 or more nucleotides in length. In some instances, a linker label sequence is 12 nucleotides in length. A linker label sequence may be used to facilitate the synthesis of the molecular barcode. The linker label can comprise an error-correcting (e.g., Hamming) code.

Solid Supports and Substrates

The stochastic barcodes disclosed herein can be attached to a solid support (e.g., bead, substrate). As used herein, the terms "tethered", "attached", and "immobilized" are used interchangeably, and may refer to covalent or non-covalent means for attaching stochastic barcodes to a solid support. Any of a variety of different solid supports may be used as solid supports for attaching pre-synthesized stochastic barcodes or for in situ solid-phase synthesis of stochastic barcode.

In some instances, a solid support is a bead. A bead may encompass any type of solid, porous, or hollow sphere, ball, bearing, cylinder, or other similar configuration composed of plastic, ceramic, metal, or polymeric material onto which a nucleic acid may be immobilized (e.g., covalently or non-covalently). A bead can, in some embodiments, comprise a discrete particle that may be spherical (e.g., microspheres) or have a non-spherical or irregular shape, such as cubic, cuboid, pyramidal, cylindrical, conical, oblong, or disc-shaped, and the like. A bead may be non-spherical in shape.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, sepharose, agarose, hydrogel, polymer, cellulose, nylon, and any combination thereof.

The diameter of the beads can, in some embodiments, be at least about 5 μm, 10 μm, 20 μm, 25 μm, 30 μm, 35 μm, 40 μm, 45 μm or 50 μm. The diameter of the beads can, in some embodiments, be at most about 5 μm, 10 μm, 20 μm, 25 μm, 30 μm, 35 μm, 40 μm, 45 μm or 50 μm. The diameter of the bead may be related to the diameter of the wells of the substrate. For example, the diameter of the bead may be at least 10, 20, 30, 40, 50, 60, 70, 80, 90 or 100% longer or shorter than the diameter of the well. The diameter of the bead can, in some embodiments, be at most 10, 20, 30, 40, 50, 60, 70, 80, 90 or 100% longer or shorter than the diameter of the well. The diameter of the bead may be related to the diameter of a cell (e.g., a single cell entrapped by the a well of the substrate). The diameter of the bead may be at least 10, 20, 30, 40, 50, 60, 70, 80, 90, 100, 150, 200, 250, or 300% or more longer or shorter than the diameter of the cell. The diameter of the bead may be at most 10, 20, 30, 40, 50, 60, 70, 80, 90, 100, 150, 200, 250, or 300% or more longer or shorter than the diameter of the cell.

A bead can, in some embodiments, be attached to and/or embedded in a substrate of the disclosure. A bead may be attached to and/or embedded in a gel, hydrogel, polymer and/or matrix. The spatial position of a bead within a substrate (e.g., gel, matrix, scaffold, or polymer) may be identified using the spatial label present on the stochastic barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligodT conjugated beads, silica beads, silica-like beads, anti-biotin microbead, anti-fluorochrome microbead, and BcMag™ Carboxy-Terminated Magnetic Beads.

A bead can, in some embodiments, be associated with (e.g. impregnated with) quantum dots or fluorescent dyes to make it fluorescent in one fluorescence optical channel or multiple optical channels. A bead may be associated with iron oxide or chromium oxide to make it paramagnetic or ferromagnetic. Beads can be identifiable. A bead can be imaged using a camera. A bead can have a detectable code associated with the bead. For example, a bead can comprise an RFID tag. A bead can comprise any detectable tag (e.g., UPC code, electronic barcode, etched identifier). A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the solid supports (e.g., beads).

A solid support may refer to an insoluble, semi-soluble, or insoluble material. A solid support may be referred to as "functionalized" when it includes a linker, a scaffold, a building block, or other reactive moiety attached thereto, whereas a solid support may be "nonfunctionalized" when it lack such a reactive moiety attached thereto. The solid support may be employed free in solution, such as in a microtiter well format; in a flow-through format, such as in a column; or in a dipstick.

The solid support can, in some embodiments, comprise a membrane, paper, plastic, coated surface, flat surface, glass, slide, chip, or any combination thereof. A solid support may take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

A solid support can be a biological molecule. For example a solid support can be a nucleic acid, a protein, an antibody, a histone, a cellular compartment, a lipid, a carbohydrate, and the like. Solid supports that are biological molecules can be amplified, translated, transcribed, degraded, and/or modified (e.g., pegylated, sumoylated, acetylated, methylated). A solid support that is a biological molecule can provide spatial and time information in addition to the spatial label that is attached to the biological molecule. For example, a biological molecule can comprise a first confirmation when unmodified, but can change to a second confirmation when modified. The different conformations can expose stochastic barcodes of the disclosure to targets. For example, a biological molecule can comprise stochastic barcodes that are inaccessible due to folding of the biological molecule. Upon modification of the biological molecule (e.g., acetylation), the biological molecule can change conformation to expose the stochastic labels. The timing of the modification can provide another time dimension to the method of stochastic barcoding of the disclosure.

In another example, the biological molecule comprising stochastic barcodes of the disclosure can be located in the cytoplasm of a cell. Upon activation, the biological molecule can move to the nucleus, whereupon stochastic barcoding can take place. In this way, modification of the biological molecule can encode additional space-time information for the targets identified by the stochastic barcodes.

A dimension label can provide information about space-time of a biological event (e.g., cell division). For example, a dimension label can be added to a first cell, the first cell can divide generating a second daughter cell, the second daughter cell can comprise all, some or none of the dimension labels. The dimension labels can be activated in the original cell and the daughter cell. In this way, the dimension label can provide information about time of stochastic barcoded in distinct spaces.

EXAMPLES

Some aspects of the embodiments discussed above are disclosed in further detail in the following examples, which are not in any way intended to limit the scope of the present disclosure.

Figure 4:
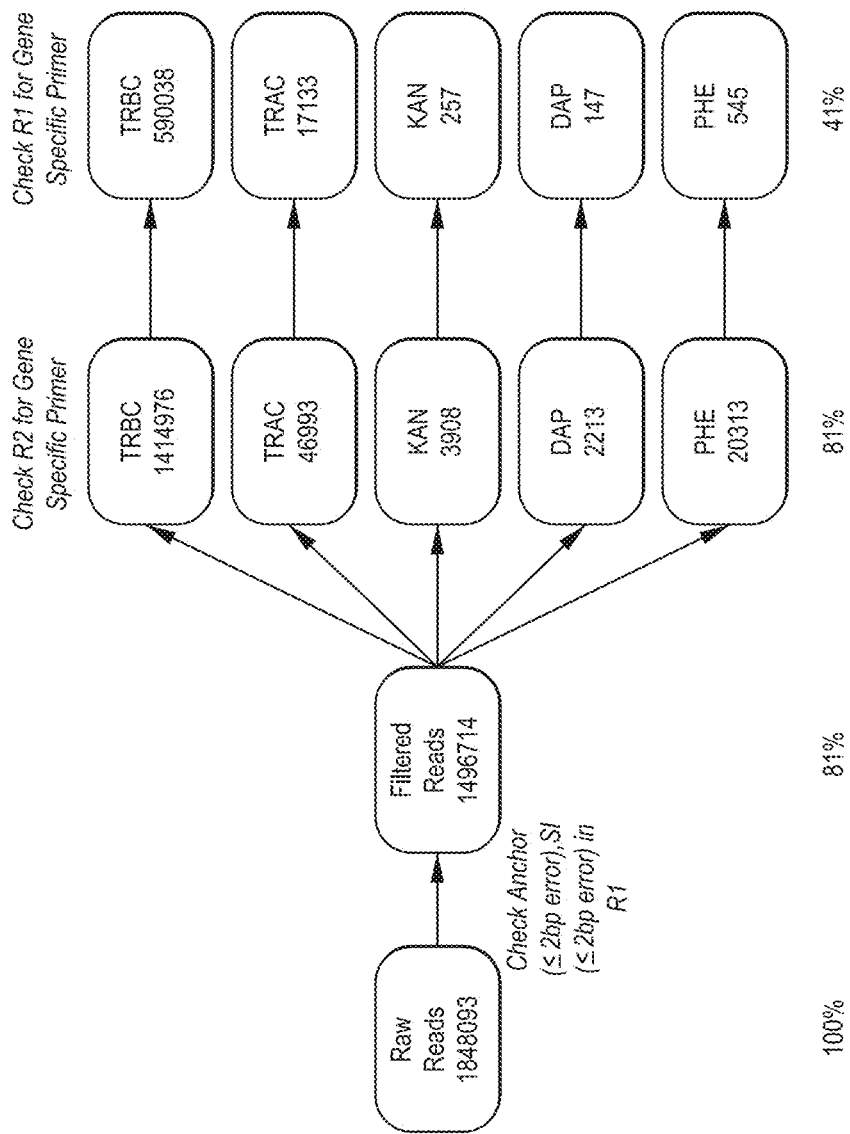
FIG. 4 shows sequencing results from 1 ng T cell RNA using the method disclosed herein.

Example 1: ES18 TCR Sequencing Run 1 ng RNA of T cell with Kan/Dap/Phe spike-in RNA was reverse transcribed using an oligonucleotide that was phosphorylated at 5' and circularization friendly comprising, from 5' to 3': a binding site for a universal primer, a sample label, a molecular label, a binding site for a P5 primer in the opposite orientation, and oligo-dT. The cDNA produced were purified using AMPure® and PCR amplified for 30 cycles using the universal primer and gene-specific primers (TCR, KDP F, Anchor R (ES29)). The PCR products were cleaned up with AMPure® and circularized using CircLigase™ I at 60° C. for 1 hr followed by 80° C. for 10 min. The circularized DNA was treated with ExoI at 37° C., 30 min, and at 80° C., 20 min. 1 µL of the treated product was PCR amplified using N1R and R primers and OneTaq® DNA polymerase. 1 µL of the PCR product was PCR amplified using P5 and P7 primers and OneTaq® DNA polymerase. The sequencing library from the last PCR step was sequenced using Illumina MiSeq v3 for 2×75 bp reads. FIG. 4 shows the results from sequencing and data analysis of the raw sequencing reads. Modified F primer mapping algorithm was used to exclude duplicated reads that map to 1+ primers.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of labeling a target nucleic acid sequence in a sample with a molecular barcode, comprising:

hybridizing an oligonucleotide comprising a molecular barcode with a first nucleic acid molecule comprising the target nucleic acid sequence, wherein the oligonucleotide specifically binds to a binding site on the first nucleic acid molecule, wherein the binding site is at least 200 nt away from the target nucleic acid sequence on the first nucleic acid molecule, wherein the oligonucleotide comprises a first universal primer binding site and a second universal primer binding site, wherein the first universal primer binding site is 5' of the molecular barcode, and wherein the second universal primer binding site is 3' of the molecular barcode;

extending the oligonucleotide to generate a second nucleic acid molecule comprising the molecular barcode and the target nucleic acid sequence;

amplifying the second nucleic acid molecule or complement thereof using a first target-specific primer and the first universal primer to generate a copy of the second nucleic acid molecule or complement thereof;

circularizing the amplified copy of the second nucleic acid molecule or complement thereof to generate a circularized nucleic acid molecule comprising the molecular barcode in close proximity to the target nucleic acid sequence;

amplifying the circularized nucleic acid molecule using the second universal primer and a second target-specific primer to generate a plurality of amplicons comprising the molecular barcode in close proximity to the target nucleic acid sequence; and sequencing the plurality of amplicons to generate a plurality of sequencing reads, wherein the sequencing reads comprise at most 200 nucleotides, wherein the sequencing reads comprise at least a portion of the target nucleic acid sequence and at least a portion of the molecular barcode.

2. The method of claim 1, further comprising synthesizing a complementary strand of the second nucleic acid molecule to generate a double-stranded nucleic acid molecule.

3. The method of claim 2, wherein the circularizing comprises circularizing amplified copy of the double-stranded nucleic acid molecule.

4. The method of claim 1, wherein the target nucleic acid sequence comprises an unknown sequence.

5. The method of claim 1, wherein the first nucleic acid is an mRNA.

6. The method of claim 1, further comprising aligning the plurality of sequencing reads to determine the full length target nucleic acid sequence.

7. The method of claim 1, wherein the binding site is a gene-specific sequence.

8. The method of claim 1, wherein the binding site is a poly-A sequence.

9. The method of claim 1, wherein the target nucleic acid sequence is 20 nt to 500 nt in length.

10. The method of claim 1, wherein the first nucleic acid molecule comprises a T cell receptor gene or an immunoglobulin gene.

11. The method of claim 1, wherein the target nucleic acid sequence comprises a complementarity determining region (CDR) coding region of a T cell receptor gene or an immunoglobulin gene.

12. The method of claim 1, wherein the target nucleic acid sequence comprises a mutation site, a splicing junction, a coding region, an untranslated region, or any combination thereof.

13. The method of claim 1, wherein the binding site is at least 500 nt away from the target nucleic acid sequence on the first nucleic acid molecule.

14. The method of claim 1, wherein the sample comprises a single cell.

15. The method of claim 14, wherein the single cell is an immune cell.

16. The method of claim 1, wherein the molecular barcode comprises a sample label, a cellular label, a molecular label, or a combination thereof.

17. The method of claim 1, wherein the binding site is at least 1,000 nt away from the target nucleic acid sequence on the first nucleic acid molecule.

18. The method of claim 1, wherein the binding site is at least 2,000 nt away from the target nucleic acid sequence on the first nucleic acid molecule.

19. The method of claim 1, wherein the second universal primer binding site is oriented in the opposite direction of the oligonucleotide.

* * * * *